United States Patent
Chaffin et al.

(10) Patent No.: US 9,220,888 B2
(45) Date of Patent: Dec. 29, 2015

(54) MEDICAL LEADS

(71) Applicant: Medtronic, Inc., Minneapolis, MN (US)

(72) Inventors: Kimberly A. Chaffin, Woodbury, MN (US); Matthew Jolly, Minneapolis, MN (US); Darrel F. Untereker, Oak Grove, MN (US); Adam J. Buckalew, Medina, MN (US); Xiangji Chen, Woodbury, MN (US); Thomas P. Grailer, Ramsey, MN (US); Julie Alkatout, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/789,602

(22) Filed: Mar. 7, 2013

(65) Prior Publication Data

US 2013/0261715 A1  Oct. 3, 2013

Related U.S. Application Data

(60) Provisional application No. 61/619,078, filed on Apr. 2, 2012, provisional application No. 61/725,361, filed on Nov. 12, 2012, provisional application No. 61/725,364, filed on Nov. 12, 2012.

(51) Int. Cl.
   *A61N 1/05* (2006.01)
   *A61L 29/06* (2006.01)
   *A61L 31/06* (2006.01)

(52) U.S. Cl.
   CPC .............. *A61N 1/0526* (2013.01); *A61L 29/06* (2013.01); *A61L 31/06* (2013.01); *A61N 1/05* (2013.01)

(58) Field of Classification Search
   None
   See application file for complete search history.

(56) References Cited

U.S. PATENT DOCUMENTS

| | | |
|---|---|---|
| 4,243,818 A | 1/1981 | Rogier |
| 4,497,326 A | 2/1985 | Curry |
| 4,947,866 A | 8/1990 | Lessar et al. |
| 5,058,584 A | 10/1991 | Bourgeois |
| 5,282,468 A | 2/1994 | Klepinski |
| 5,303,704 A | 4/1994 | Molacek et al. |
| 5,428,123 A | 6/1995 | Ward et al. |
| 5,443,492 A | 8/1995 | Stokes et al. |
| 5,589,563 A | 12/1996 | Ward et al. |
| 5,628,778 A | 5/1997 | Kruse et al. |
| 5,865,843 A | 2/1999 | Baudino |
| 5,922,014 A | 7/1999 | Warman et al. |
| 5,999,858 A | 12/1999 | Sommer et al. |
| 6,149,678 A | 11/2000 | DiDomenico et al. |

(Continued)

FOREIGN PATENT DOCUMENTS

| WO | WO 98/13405 | 4/1998 |
|---|---|---|
| WO | WO 99/53994 | 10/1999 |

(Continued)

OTHER PUBLICATIONS

Thermoplastic Silicone-Urethane Copolymers: A New Class of Biomedical Elastomers, Medical Devices & Diagnostic Industry Magazine, Apr. 1, 2000.*

(Continued)

*Primary Examiner* — Paula J Stice
(74) *Attorney, Agent, or Firm* — Carol F. Barry

(57) ABSTRACT

Medical leads, such as medical electrical leads and medical neurological leads, that include a polymeric material that includes a silicone-urethane-containing polymer having improved hydrolytic stability.

33 Claims, 9 Drawing Sheets

(56) References Cited

U.S. PATENT DOCUMENTS

| | | | |
|---|---|---|---|
| 6,313,254 | B1 | 11/2001 | Meijs et al. |
| 6,420,452 | B1 | 7/2002 | Gunatillake et al. |
| 6,437,073 | B1 | 8/2002 | Gunatillake et al. |
| 6,627,724 | B2 | 9/2003 | Meijs et al. |
| 6,785,576 | B2 | 8/2004 | Verness |
| 6,858,680 | B2 | 2/2005 | Gunatillake et al. |
| 6,984,700 | B2 | 1/2006 | Benz et al. |
| 7,026,423 | B2 | 4/2006 | Gunatillake et al. |
| 7,101,956 | B2 | 9/2006 | Benz et al. |
| 7,184,838 | B2 | 2/2007 | Cross, Jr. |
| 7,365,134 | B2 | 4/2008 | Benz et al. |
| 7,452,377 | B2 | 11/2008 | Watling et al. |
| 7,715,922 | B1 * | 5/2010 | Tan ............... 607/116 |
| 7,860,580 | B2 | 12/2010 | Falk et al. |
| 8,027,737 | B2 | 9/2011 | Kokones et al. |
| 8,116,880 | B2 | 2/2012 | Cross, Jr. |
| 8,155,759 | B2 | 4/2012 | Pinchuk |
| 8,166,880 | B2 | 5/2012 | Lafont |
| 8,324,290 | B2 | 12/2012 | Desai et al. |
| 8,374,704 | B2 | 2/2013 | Desai et al. |
| 8,512,312 | B2 | 8/2013 | Sage |
| 8,644,952 | B2 | 2/2014 | Desai et al. |
| 8,674,035 | B2 | 3/2014 | Padsalgikar |
| 8,765,895 | B2 | 7/2014 | Zhou et al. |
| 2004/0054113 | A1 | 3/2004 | Benz et al. |
| 2007/0027285 | A1 | 2/2007 | Gunatillake et al. |
| 2010/0076538 | A1 | 3/2010 | Desai et al. |
| 2011/0196464 | A1 | 8/2011 | Pinchuk |
| 2012/0245533 | A1 | 9/2012 | Morris et al. |

FOREIGN PATENT DOCUMENTS

| | | |
|---|---|---|
| WO | WO 2008/066914 A1 | 6/2008 |
| WO | WO 2009/061534 A1 | 5/2009 |
| WO | WO 2011/050396 A1 | 5/2011 |
| WO | WO 2011/099994 A1 | 8/2011 |
| WO | WO 2013/151656 A1 | 10/2013 |

OTHER PUBLICATIONS (PCT/US2013/029725) PCT Notification of Transmittal of the International Search Report and the Written Opinion of the International Searching Authority.

Gunatillake et al., "Poly(dimethylsiloxane)/Poly(hexamethylene oxide) Mixed Macrodiol Based Polyurethane Elastomers. I. Synthesis and Properties," *J. App. Poly. Sci.*, 2000; 76:2026-2040.

Martin et al., "Polydimethylsiloxane/polyether-mixed macrodial-based polyurethane elastomer: biostability,"*Biomaterials*, 2000;21:1021-1029.

Simmons et al., "The effect of sterilization on a poly(dimethylsiloxane)/poly(hexamethylene oxide) mixed macrodiol-based polyurethane elastomer," *Biomaterials*, 2006;27:4485-4497.

International Preliminary Report on Patentability, issued Oct. 16, 2014, Patent Application No. PCT/US2013/029725, filed Mar. 7, 2013.

Chaffin et al., "Influence of Water on the Structure and Properties of PDMS-Containing Multiblock Polyurethanes," *Macromolecules*, 2012; 45(22)9110-9120.

Chaffin et al., "Supporting Information for: Influence of Water on the Structure and Properties of PDMS-Containing Multiblock Polyurethanes," 2012; 15 pages. ("Influence of Water on the Structure and Properties of PDMS-Containing Multiblock Polyurethanes," Macromolecules, 2012; 45(22)9110-9120).

Chaffin et al., "Polyether Urethane Hydrolytic Stability after Exposure to Deoxygenated Water," *Macromolecules*, 2014; 47(15)5220-5226.

*Compositional and Failure Analysis of Polymers: A Practical Approach*, Schiers, Wiley, 2000, England, Chapter 13, Chemical attack of polymers, pp. 365-366.

Garrido et al., "*In Vivo* Degradation of Silicones," *Magnetic Resonance in Medicine*, 1993; 29(6):839-843.

Graiver et al., "A Review of the Fate and Effects of Silicones in the Environment," *Journal of Polymers and the Environment*, Oct. 2003; 11(4):129136.

Kaali, et al., "Degradation of biomedical polydimethylsiloxanes during exposure to in vivo biofilm environment monitored by FE-SEM, ATR-FTIR, and MALDI-TOF MS" *Journal of Applied Polymer Science*, 2010; 115(2):802-810.

Keshavaraj et al., "Effects of moisture on structural silicone rubber sealants used in window glazing application," *Construction and Building Materials*, Dec. 1994; 8(4):227.

Kole et al., "Accelerated Hydrothermal Weathering of Silicone Rubber, EPDM, and Their Blends," *Journal of Applied Polymer Science*, Nov. 1994; 54(9):1329-1337.

Lahiouhel et al., "A telechelic fluorinated diol from 1,6-diiodoperfluorohexane," *Journal of Fluorine Chemistry*, 2001; 107(1):81-88.

Lyu et al., "Kinetics and Time—Temperature Equivalence of Polymer Degradation," *Biomacromolecules*, 2007; 8(7):2301-2311.

Pfleiderer et al., "Migration and Biodegradation of Free Silicone from Silicone Gel-Filled Implants after Long-Term Implantation," *Magnetic Resonance in Medicine*, 1993; 30(5):534-543.

Pfleiderer et al., "Biodegradation of polysiloxanes in lymph nodes of rats measured with $^{29}$Si NMR," Biomaterials, 1999; 20(6):561-571.

Polymer Degradation and Stabilisation, Grassie and Scott, Cambridge University Press, Cambridge, 1985. pp. 222.

Schwendeman et al., "Synthesis of Amorphous Hydrophobic Telechelic Hydrocarbon Diols via Admet Polymerization," *Macromolecular Chemistry and Physics*, 2009; 210(21):1818-1833.

Spivack et al., "Hydrolysis of Oligodimethylsiloxane-α,ω-diols and the Position of Hydrolytic Equilibrium," *Environ. Sci. Technol.*, 1994; 28:2345-2352.

West, "Theoretical analysis of hydrolysis of polydimethylsiloxane (PDMS)," *Journal of Biomedical Materials Research*, 1997; 35:505-511.

Yilgor et al. "Reactive Difunctional Siloxane Oligomers, Synthesis and Characterization," *Polym. Mater. Sci. Eng.*, 1984; 50:518-522.

* cited by examiner

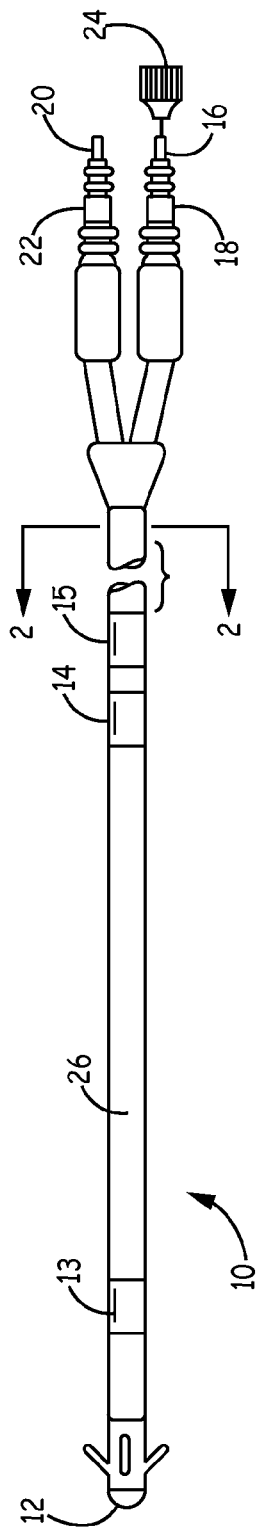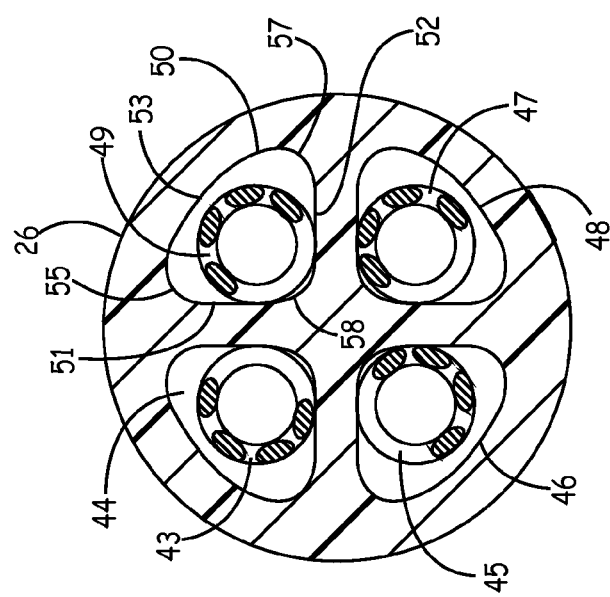
FIG. 1
FIG. 2

MEDICAL LEADS

CROSS-CITE TO RELATED APPLICATIONS

The present application claims priority to U.S. Provisional Application No. 61/619,078, filed on Apr. 2, 2012, U.S. Provisional Application No. 61/725,361, filed on Nov. 12, 2012, and U.S. Provisional Application No. 61/725,364, filed on Nov. 12, 2012, all of which are incorporated herein by reference.

BACKGROUND OF THE INVENTION

Silicone-urethane polymers (i.e., silicone-polyurethanes or polydimethylsiloxane-polyurethanes) are a class of materials that was developed to fill the need for soft biostable materials needed in implantable medical devices. Such materials are commercially available from sources such as Aortech (e.g., under the tradename Elast-Eon E2A) and DSM (e.g., under the tradename PurSil 35). The entire industry believed that this was the answer to the need for oxidatively stable materials. It was generally believed that because silicone-polyurethanes as a class of materials were considered primarily polyurethane, this improved oxidative stability was sufficient for many uses.

SUMMARY OF THE INVENTION

The present invention is directed to the discovery that degradation of a class of silicone-urethane polymeric materials developed for use in implantable medical devices occurs hydrolytically, even though it was thought such materials were oxidatively stabilized. Such discovery has led to the development of new materials that have improved hydrolytic stability. Thus, the present disclosure provides a medical lead with a polymeric material that has improved hydrolytic stability.

In one embodiment, the present disclosure provides a medical lead that includes an elongated lead body including a polymeric material, wherein the polymeric material includes a silicone-urethane polymer having hydrolytic stability greater than that of a Reference Polymer X, a Reference Polymer Y, or both Reference Polymers X and Y. The medical lead can be in the form of a medical electrical or neurological lead.

In one embodiment, the present disclosure provides a medical electrical lead, including: an elongated lead body having a first lumen, extending longitudinally along said lead body; and a conductor (e.g., coiled conductor) located within and extending longitudinally along said lumen; wherein the lead body includes a polymeric material (particularly insulation material), wherein the polymeric material includes a silicone-urethane polymer having hydrolytic stability greater than that of a Reference Polymer X, a Reference Polymer Y, or both Reference Polymers X and Y.

In one embodiment, the present disclosure provides a medical, neurological lead for use in electrical signaling and/or drug delivery. The lead includes: an elongated body with a distal portion, a central portion and a proximal portion; wherein the body includes delivery means extending to said distal portion; and wherein the lead body includes a polymeric material (particularly insulation material), wherein the polymeric material includes a silicone-urethane polymer having hydrolytic stability greater than that of a Reference Polymer X, a Reference Polymer Y, or both Reference Polymers X and Y.

In certain embodiments, the delivery means includes electrical signal delivery means. Preferably, the electrical signal delivery means is an implantable lead having at least one electrode. In certain embodiments, the delivery means includes drug delivery means. Preferably, the drug delivery means includes a catheter.

Herein, "Reference Polymer X" is a silicone-urethane polymer (i.e., silicone-polyurethane) with a soft and hard segment weight ratio of 60/40, respectively, with the soft segment containing 80 wt-% PDMS (molecular weight approximately 1000 Da, n=10-11 repeat units) and 20 wt-% PTMO (molecular weight approximately 1000 Da) and the hard segment comprised of BDO (1,4-butanediol) and MDI (4,4'-methylene diphenyl diisocyanate). Reference Polymer X is available commercially as PurSil 35 from DSM Biomedical.

Herein, "Reference Polymer Y" is a silicone-urethane polymer (i.e., silicone-polyurethane) with a soft and hard segment weight ratio of 60/40, respectively, with the soft segment containing 80 wt-% PDMS (molecular weight approximately 1000 Da, n=10-11 repeat units) and 20 wt-% PHMO (molecular weight approximately 700 Da) and the hard segment comprised of BDO (1,4-butanediol) and MDI (4,4'-methylene diphenyl diisocyanate). Reference Polymer Y is available commercially as Elast-Eon E2A from Aortech Int.

In certain embodiments, the silicone-urethane polymer can be prepared from one or more polydialkyl-, polydiaryl-, or polyalkylaryl-siloxane monomers other than a polydimethylsiloxane monomer.

In certain embodiments, the silicone-urethane polymer can be prepared from a mixture of one or more polydimethylsiloxane monomers and at least one other monomer selected from polydialkyl-, polydiaryl-, and polyalkylaryl-siloxane monomers other than a polydimethylsiloxane monomer.

In certain embodiments, the silicone-urethane polymer can be prepared from a polydimethylsiloxane diol monomer with a number average molecular weight equal to or higher (preferably higher) than 1000 Da. In certain embodiments, the silicone-urethane polymer can be prepared from a polydimethylsiloxane diol monomer with a number average molecular weight equal to or higher than 1500 Da. In certain embodiments, the silicone-urethane polymer can be prepared from a polydimethyl siloxane diol monomer with a number average molecular weight equal to or higher than 2000 Da.

In certain embodiments, the silicone-urethane polymer can be prepared from a polydimethyl siloxane diol monomer of the formula:

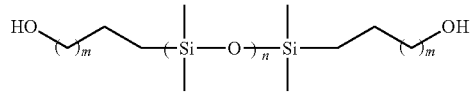

wherein n is from 10 to 1500 and m is from 0 to 18 (preferably n is from 15 to 150 and m is from 5 to 18, and more preferably n is from 20 to 150 and m is 10 to 18).

In certain embodiments, the silicone-urethane polymer can be prepared from a PDMS (polydimethyl siloxane) diol with hydrophobic end groups/blocks. In certain embodiments, the PDMS diol with hydrophobic end groups can be prepared from a hydride-terminated siloxane and an unsaturated alcohol selected from the group of 9-decen-1-ol, 10-undecen-1-ol, oleyl alcohol, and combinations thereof.

In certain embodiments, the silicone-urethane polymer can be prepared from a hydrophobic co-soft segment and/or chain extender.

In certain embodiments, the silicone-urethane polymer is crosslinked.

The terms "comprises" and variations thereof do not have a limiting meaning where these terms appear in the description and claims.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise. The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

When a group is present more than once in a formula described herein, each group is "independently" selected, whether specifically stated or not. For example, when more than one R group is present in a formula, each R group is independently selected.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

In the drawings where like numerals refer to like components throughout several views:

FIG. 1 is a diagram of a lead which incorporates a preferred embodiment of the present disclosure.

FIG. 2 is a cross-sectional view of the lead body of the lead shown in FIG. 1.

DETAILED DESCRIPTION OF PREFERRED EMBODIMENTS

Figure 3:
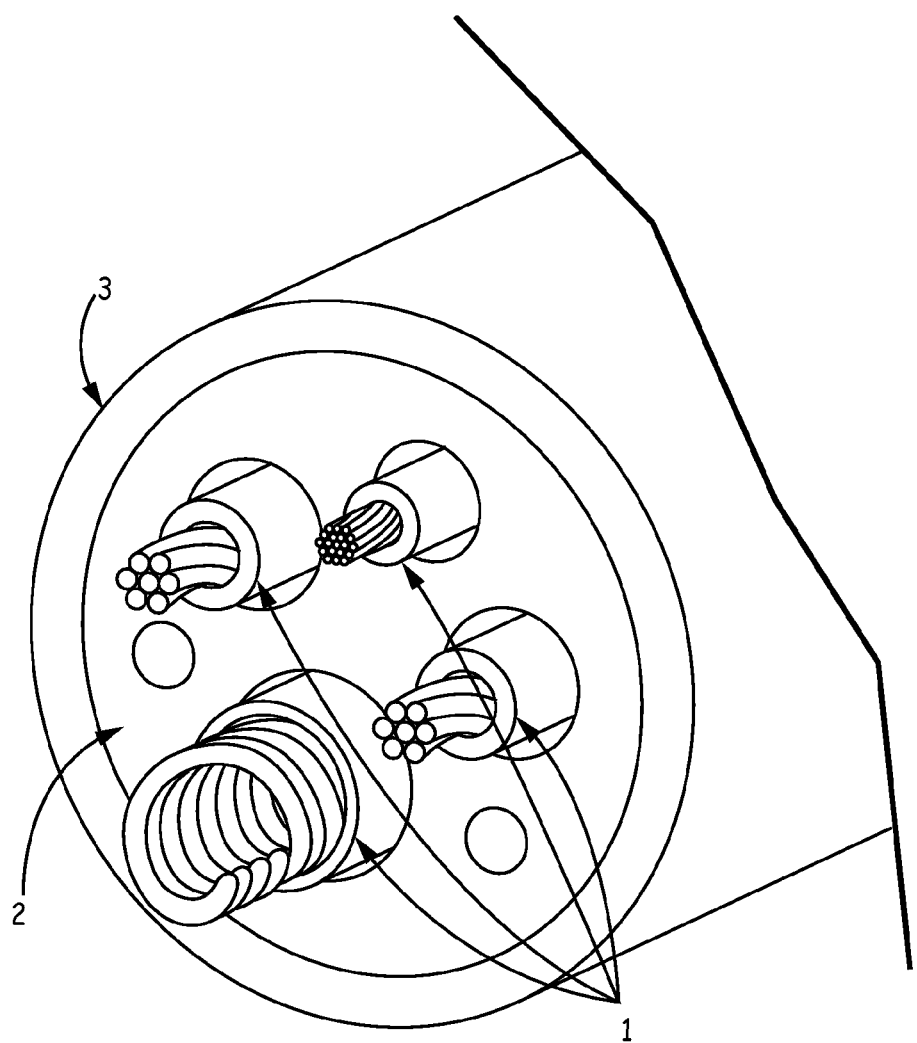
FIG. 3 is a cross-section of an exemplary lead body.

It has been previously believed that polymer degradation in an implantable medical device occurs predominately by oxidation. Mechanisms for stabilizing polymers against oxidative degradation have been incorporated into such polymers; however, it has been discovered that hydrolytic degradation still occurs. Thus, the present invention provides a medical lead (e.g., electrical or neurological lead) with a polymeric material that has improved hydrolytic stability.

Medical leads are used to transmit electrical signals to and from medical devices such as pacemakers and neurostimulators, for example. The lead body is usually made from a piece of polymeric tubing having a round cross-section exterior and a round cross-section lumen. Typically a coiled metallic electrical conductor having a round cross-section is placed in the lumen completely filling it. The tubing protects and insulates the conductor. The coiled conductor can usually receive a stylet to help position and place the lead during implantation. There are many examples of medical electrical leads, including, for example, those described in U.S. Pat. Nos. 6,785,576, 5,303,704, 5,999,858, 6,149,678, 4,947,866, 5,922,014, 5,628,778, 4,497,326, 5,443,492, 7,860,580, and 5,303,704.

As an exemplary embodiment of a medical electrical lead, FIG. 1 is a diagram of a lead assembly 10, which incorporates a preferred embodiment of the invention. The lead body 26 carries four electrodes including ventricular electrodes 12 and 13 and atrial electrodes 14 and 15. Within the lead body are four conductors, one coupled to each of the electrodes and extending proximally to a corresponding electrical connector. The proximal end of the lead assembly 10 has a dual in-line connector assembly including connector pin 16, coupled to electrode 12, connector ring 18, coupled to electrode 13, connector pin 20, coupled to electrode 14 and connector ring 22, coupled to electrode 15. A stylet 24 may be inserted into the lead through pin 16 to stiffen it as an aid to implantation.

Lead body 26 in FIG. 1 is preferably fabricated of silicone rubber, polyurethane or other implantable polymer. In particular, lead body 26 is preferably fabricated of a polymer of the present disclosure.

Electrodes 12, 13, 14, and 15 in FIG. 1 are preferably fabricated of platinum alloy or other biocompatible metal. Connectors 16, 18, 20, and 22 are preferably fabricated of stainless steel or other biocompatible metal.

As illustrated the lead includes electrodes which may serve as means for delivery of stimulation pulses and as means for sensing physiological electrical signals. It should also be understood that a lead according to the present invention may also include means for sensing other physiological parameters, such as pressure, oxygen saturation, temperature, or pH. The lead may include electrodes only, other physiologic sensors only, or a combination of both.

FIG. 2 is a cross-section through the lead body 26. In this view, it can be seen that lead body 26 is provided with four pie-shaped or generally triangular lumens. The first lumen 44 contains a first coiled conductor 43. The second lumen 46 contains a second coiled conductor 45. The third lumen 48 contains a third coiled conductor 47. The fourth lumen 50 contains a fourth coiled conductor 49. The conductors 43, 45, 47, and 49 are preferably fabricated of MP35N alloy or other biocompatible metal. In the drawing each coiled conductor is shown as a multi-filar coil. However monofilar coils are useful as well. One of the four conductors is coupled to pin 16 and also serves to receive a stylet.

The lead body may employ the multi-lumen configuration illustrated over its entire length, with two of the lumens unused distal to electrodes 14 and 15. Alternatively, a transition to a lead body having a coaxial or side by side two-lumen configuration as typically used in bipolar pacing leads may occur at or distal to electrodes 14 and 15. As seen in cross section, the representative fourth lumen 50 has three walls each having a radius of curvature substantially greater than the radius of curvature of the conductor coil. These walls include two substantially planar walls 51 and 52 each extending along a radius of the body and an outer curved wall 53, extending along the outer circumference of the lead body. The walls are joined to one another along corners 55, 57, and 58 each of which have a radius of curvature substantially less than the radius of curvature of the conductor coils, as seen in this cross-section.

In certain embodiments, contact between a coil of a conductor and the inner surface of a lumen will be limited to those portions of the inner surfaces of the lumen which have a substantially greater radius of curvature than the conductor coil. Contact will thus be limited to discrete points of contact, rather than along substantial lengths of the individual coils, as would occur in prior leads employing circular coils and circular lumens of similar sizes. Contact will occur only along walls 51, 52 and 53, and not in corners 55, 57 and 59. Along the length of the lead, individual coils will contact various points on all three walls 51, 52, and 53.

The present medical electrical lead includes a polymeric material of the present disclosure as part or all of lead body 26, but theoretically this could apply to any insulator on the lead body.

FIG. 3 is a cross-section of another exemplary lead body showing several insulation layers: a primary insulation layer 1, which encapsulates the conductors; a secondary insulation layer 2, which contains the lumens for the conductors; and a tertiary outer insulation layer 3. The silicone polyurethane polymer of this disclosure forms part or all of any of these insulation layers.

Medical, neurological leads are used for insertion into the human body, for transmission of therapeutic drugs and/or electrical signals to body organs such as the spinal cord or brain, for acute and chronic pain relief, acute and chronic treatment of disease, and the like. The leads are used in programmable, electronic, implantable devices which deliver drugs and/or electrical stimulation in programs of therapy for the benefit of mankind.

Implantable electrical devices are capable of relieving chronic, inoperable pain by interfering with the transmission of pain signals in the spinal cord and brain. Implantable drug delivery devices are capable of delivering pain relieving drugs to the same dramatic effect. Both types of devices are also capable of new therapies for treatment of a variety of diseases. An advantage of the electrical devices is that typically no drugs are necessary. With the drug delivery devices, an advantage is that drug dosages are reduced relative to other therapies because the drugs are delivered directly to desired locations of therapy, rather than in remote locations such as the blood vessels of the extremities, and without concern for bodily elimination or chemical interaction.

With the electrical devices, electrical stimulation is typically delivered from the devices to the body through wired leads, to electrodes. The electrodes are located on and exposed to the body on the distal extremity of the leads, and the leads typically extend into and along the epidural space of the spinal cord, or into the brain at surgically drilled boreholes. The leads may also be subcutaneous where necessary. As an example, leads may extend from devices implanted above the clavicles, under the skin, to a bore hole atop the skull, and thence deep into brain tissue.

With the drug delivery devices, catheters, which for purposes of this description are also considered "neurological leads," extend in similar ways. Leads in the described applications are typically smooth walled, plastic, tubular members, although variation is possible.

There are many examples of medical neurological leads, including, for example, those described in U.S. Pat. Nos. 5,058,584, 5,865,843, U.S. Pat. Pub. No. 2008/0275429. Medical neurological leads include, for example, paddle leads such as disclosed in U.S. Pat. No. 8,166,880, in-line cylindrical leads such as disclosed in U.S. Pat. No. 7,184,838, and drug delivery catheters such as disclosed in U.S. Pat. Pub. No. 2012/0245533. These leads/catheters can be placed in numerous locations. Electrode leads are used in the epidural space, within the brain itself, in the sacral root, and within blood vessels. Cuff type electrodes, as in U.S. Pat. No. 5,282,468, can be mounted around nerve bundles or fibers. Drug delivery catheters can be placed in/adjacent the spinal column or any location within the vascular system.

The polymeric material of the present disclosure may be used as all or part of the lead body, as insulation, as an inner or outer layer, etc.

Figure 4:
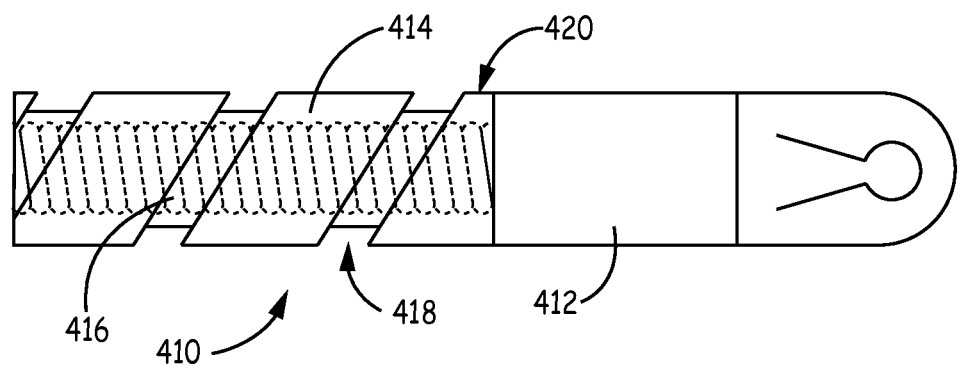
FIG. 4 is a diagram of a neurological electrical lead which incorporates a preferred embodiment of the present disclosure.
Figure 5:
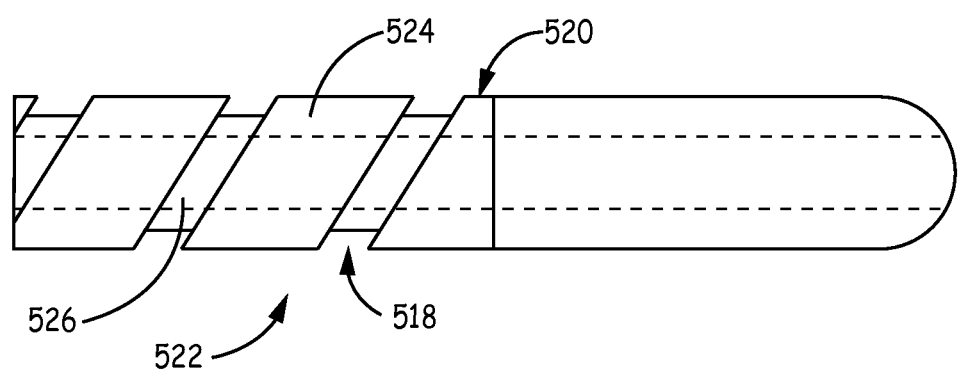
FIG. 5 is a diagram of a neurological drug delivery lead which incorporates a preferred embodiment of the present disclosure.

Referring to FIGS. 4 and 5, an exemplary lead of the disclosure includes a distal portion 10, and associated central and proximal portions not shown. As known to persons of ordinary skill in the art, if electrical, the lead may connect to an electrical signal generating device (hereafter "a signal generator") which may or may not be implantable in whole or in part into the human body. If the lead is a drug delivery lead, the lead may connect to a drug pump, which also may or may not be implantable. In either case, the lead is intended to have at least a portion engaged in the tissue of the body. Depending on the application, the lead may engage tissue in the proximal, central, or distal portions of the lead. The lead may or may not enter the epidural space which surrounds the spinal cord, or the lead may enter the brain through the skull. Generally, the lead is substantially elongated, with the dimension of its length one hundred or more times the dimension of its width.

Again if electrical, as in FIG. 4, the lead 410 may include one or more electrodes, such as an electrode designated 412. The electrode may be annular, surrounding the lead body, or in other shape or form. If a drug delivery lead, as in FIG. 5, the lead 522 may include one or more openings for transmission of drugs from the drug pump to the body, in the place of electrodes, or in addition to electrodes.

The lead 410 or 522 is desirably, generally circular in cross-section, although variations are within contemplation. Focusing on an electrical lead of FIG. 4, for illustration, an insulating, annular, external lead sheath or body 414 surrounds an electrically transmissive internal core 416, shown in phantom. The core 416 frequently takes the form of a helically wound or coiled wire, interconnected to the distal electrode(s) and the proximal signal generator. The wire has a direction of its winding, which is right hand or left hand, clockwise or counterclockwise. As desired, although not presently contemplated, the lead may also include additional intermediate or other layers, or other components.

FIG. 4. shows an electrical lead having a helical groove 418, and associated helical land 420. FIG. 5 shows a drug deliver lead or catheter having a liquid insulating, annular, external lead sheath or body 524 surrounds a liquid transmissive internal and open core or passage 526, shown in phantom.

Polymers of the present disclosure are elastomers. An "elastomer" is a polymer that is capable of being stretched to approximately twice its original length and retracting to approximately its original length upon release. Polymers of the present disclosure can be made of two or more different monomers. They can be random, alternating, block, star-block, segmented copolymers, or combinations thereof. Preferably, the polymers are segmented copolymers (i.e., containing a multiplicity of both hard and soft domains or segments on any polymer chain) and are comprised substantially of alternating relatively soft segments and relatively hard segments.

As used herein, a "hard" segment is one that is crystalline at use temperature, or amorphous with a glass transition temperature above use temperature, or when in the water saturated state at body temperature, a hard segment has a Tg of about 30° C. (below body temperature, but above that of the soft segments −100° C. to −30° C.), and a "soft" segment is one that is amorphous with a glass transition temperature below use temperature (i.e., rubbery). A crystalline or glassy moiety or hard segment is one that adds considerable strength and higher modulus to the polymer. Similarly, a rubbery moiety or soft segment is one that adds flexibility and lower modulus, but may add strength particularly if it undergoes strain crystallization, for example. The random or alternating soft and hard segments are linked by urethane groups and the polymers may be terminated by hydroxyl, amine, and/or isocyanate groups or surface modified end groups.

Certain of the segments, either the hard or the soft segments, or both, can include a silicone-containing moiety. The presence of the silicone-containing moiety provides a polymer that is typically more resistant to oxidation because it displaces some of the oxidatively susceptible ether soft segments if a polymer with comparable hardness is targeted but still has a relatively low glass transition temperature (Tg). Furthermore, preferably, both the hard and soft segments are themselves substantially ether-free, ester-free, and carbonate-free polyurethanes. The silicone-containing groups (i.e., moieties) are of the formula —O—Si(R)$_2$—, and are typically provided by polydimethylsiloxane (PDMS). Although the use of silicone-containing groups in a polymer provides improved oxidative stability when used in an implantable medical device, this is not sufficient for hydrolytic stability.

Typically, polyurethanes are made by a process in which a diisocyanate is reacted with diol to form a prepolymer. The resulting prepolymer can be further reacted with a chain extender, such as a diol. To make a polysiloxane-polyurethane, the diol will typically include the polysiloxane moiety.

The present disclosure provides various mechanisms for improving hydrolytic stability of a silicone-polyurethane.

One approach is the use of PDMS diol monomers with number average molecular weights equal to or higher (preferably higher) than 1000 Da (most of the commercially available silicone urethanes include PDMS segments of 1000 daltons). In certain embodiments, the silicone-urethane polymer can be prepared from a polydimethyl siloxane diol monomer with a number average molecular weight equal to or higher than 1500 Da. In certain embodiments, the silicone-urethane polymer can be prepared from a polydimethyl siloxane diol monomer with a number average molecular weight equal to or higher than 2000 Da.

In some embodiments, suitable PDMS monomers are of the formula:

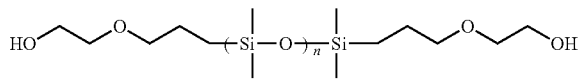

wherein 10<n<1500.

In some embodiments, suitable PDMS monomers are of the formula:

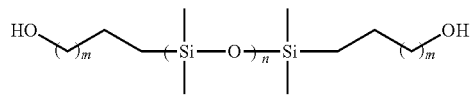

wherein n is from 10 to 1500 and m is from 0 to 18 (preferably n is from 15 to 1500, or 15 to 150, and m is from 5 to 18, and even more preferably n is from 20 to 1500, or 20 to 150, and m is 10 to 18).

Such longer PDMS chains can contribute to the modification of the morphological phases of the polymer. For example, introduction of a new linkage between the urethane and the silicone moiety can provide a hydrophobic protective barrier to the silicone.

Another approach to slow down the hydrolysis of the siloxane bond in a silicone-polyurethane is the use of various alkyl- or aryl-siloxane monomers other than PDMS. Although many documents discuss the use of such monomers, they are not typically incorporated into any experimental or commercial materials. Generally, such monomers can be demonstrated by the following oligomeric or polymeric structure:

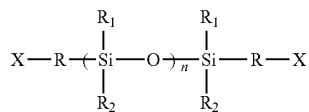

wherein, each R is independently a divalent aliphatic group, each X is independently an hydroxyl or amine group, each $R_1$ and $R_2$ are independently a C1-C4 alkyl group, phenyl, or a combination thereof, n is from 1 to 1500, with the proviso that not all $R_1$ and $R_2$ groups are methyl.

Examples of some polysiloxane homopolymers include those such as polydiethylsiloxane, polypropylsiloxane, polydibutylsiloxane, etc., and copolymers of these species. These polysiloxane contain bulky side groups and could provide the steric hindrance to retard or stop the hydrolysis reaction. Some structures, and methods of making them, are described below in the Examples Section.

Another approach to slow down the hydrolysis of silicone-polyurethane is to increase the overall hydrophobicity of the polyurethane. This can be done by introducing hydrophobic moieties into urethane at the PDMS chain end. For example, a PDMS diol with hydrophobic end groups can be prepared from a hydride-terminated polysiloxane and an unsaturated alcohol such as: 9-decen-1-ol, 10-undecen-1-ol, or oleyl alcohol.

Another way to increase the hydrophobicity of polyurethane is to use a hydrophobic co-soft segment and/or chain extender. Examples of some diols that can be used as the co-soft segment/chain extender to prepare polyurethanes are described in the Examples Section.

The silicone hydrolysis reaction may be facilitated or catalyzed by neighboring functional groups that could coordinate (hydrogen bond, dipole-dipole, etc.) and stabilize intermediate hydrolysis products during the hydrolysis reaction. For example, the PDMS species employed in commercially available silicone polyurethane formulations contains ether functionality in the PDMS chain end groups. Further neighboring urethane groups which are polar and could hydrogen bond could also coordinate to siloxane ether bonds and participate in facilitating the hydrolysis reaction. The proximity of the neighboring urethane group to the siloxane bonds could be important. By utilizing PDMS diols without coordinating groups (ether, etc.) and/or by reducing the proximity of the siloxane ether to urethane groups, for example, by introducing alkyl end groups with increased chain length, silicone polyurethanes with improved hydrolytic stability could result.

Yet another method to slow down the hydrolysis of silicone-polyurethane is to crosslink the silicone domain(s) in the polymer. Crosslinked materials are mechanically stable due to their networked structure. For example, silicone adhesive/sealant is mechanically stable for a long period time even in contact with water. In an analogous manner to this phenomenon, silicone-polyurethane with crosslinked polysiloxane moiety should have longer mechanical stability than that without crosslinking.

In contrast to a previous crosslinking method for making silicone polyurethane (US 2007/0027285 A1), which formed the crosslinked polyurethane during synthesis of polyurethane polymer, the crosslinking reaction of the present disclosure focuses on crosslinking the polyurethane after synthesis of the polyurethane polymer. Preferably, the crosslinking reaction of the PDMS soft segment is typically initiated at the extrusion process step and is completed in a post-cure process.

One approach to crosslink PDMS is to use a radical reaction, similar to the crosslinking method used in the silicone tubing. Since the polyurethane tubing is extruded at high temperature, a radical generator such as dicumyl peroxide, di-t-amyl peroxide, and di-t-butyl peroxide will be used to crosslink the PDMS domain in the polyurethane. During the extrusion, a small percentage of the peroxide is introduced into the polyurethane and mixed in the extruder. These peroxides decompose at high temperature and have reasonable half-lives at 150-160° C. This allows the PDMS domain to be crosslinked while the polyurethane is being extruded. Post-extrusion cure is also possible. Alternatively, a vinylmethylsiloxane-dimethylsiloxane copolymer or other structures can be introduced to facilitate the crosslinking. Another approach to crosslink the PDMS in the urethane is to prepare the silicone-polyurethane with polysiloxane copolymer containing crosslinkable units that will only react with each other at high temperature. For example, a copolymer of PDMS with multiple pendent benzocyclobutene (BCB) groups is used as a soft segment for making polyurethane. The crosslinked PDMS domain will maintain the mechanical properties longer than the non-crosslinked version upon the same degree of degradation (mainly hydrolysis). Additionally, the hydrophobic BCB group will decrease the water absorption in the polyurethane, which in turn slows down the hydrolysis reaction. By controlling the content of BCB in the polysiloxane oligomer, the crosslinking density can be controlled. This is discussed in greater detail in the Examples Section.

ILLUSTRATIVE EMBODIMENTS

1. A medical lead comprising an elongated lead body comprising a polymeric material, wherein the polymeric material comprises a silicone-urethane polymer having hydrolytic stability greater than that of a Reference Polymer X, a Reference Polymer Y, or both Reference Polymers X and Y.

2. The medical lead of embodiment 1 in the form of a medical electrical or neurological lead.

3. A medical electrical lead comprising:
an elongated lead body having a first lumen, extending longitudinally along said lead body; and
a conductor located within and extending longitudinally along said lumen;
wherein the lead body comprises a polymeric material, wherein the polymeric material comprises a silicone-urethane polymer having hydrolytic stability greater than that of a Reference Polymer X, a Reference Polymer Y, or both Reference Polymers X and Y.

4. A medical, neurological lead for use in electrical signaling and/or drug delivery comprising:
an elongated body with a distal portion, a central portion and a proximal portion;
wherein the body includes delivery means extending to said distal portion; and
wherein the elongated body comprises a polymeric material, wherein the polymeric material comprises a silicone-urethane polymer having hydrolytic stability greater than that of a Reference the Polymer X, a Reference Polymer Y, or both Reference Polymers X and Y.

5. The lead of embodiment 4 wherein the delivery means comprises electrical signal delivery means.

6. The lead of embodiment 5 wherein the electrical signal delivery means is an implantable lead having at least one electrode.

7. The lead of embodiment 4 wherein the delivery means comprises drug delivery means.

8. The lead of embodiment 7 wherein the drug delivery means comprises a catheter.

9. The lead of any of embodiments 1 through 8 wherein the polymeric material is polymeric insulation material.

10. The lead of any of embodiments 1 through 9 wherein the silicone-urethane polymer is prepared from one or more polydialkyl-, polydiaryl-, or polyalkylaryl-siloxane monomers other than a polydimethylsiloxane monomer.

11. The lead of any of embodiments 1 through 9 wherein the silicone-urethane polymer is prepared from a mixture of one or more polydimethylsiloxane monomers and at least one other monomer selected from polydialkyl-, polydiaryl-, and polyalkylaryl-siloxane monomers other than a polydimethylsiloxane monomer.

12. The lead of any of embodiments 1 through 9 wherein the silicone-urethane polymer is prepared from a polydimethyl siloxane diol monomer with a number average molecular weight equal to or higher than 1000 Da.

13. The lead of any of embodiments 1 through 9 wherein the silicone-urethane polymer is prepared from a polydimethyl siloxane diol monomer of the formula:

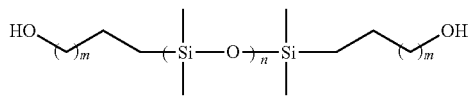

wherein n is from 10 to 1500 and m is from 0 to 18.

14. The lead of embodiment 13 wherein n is from 15 to 1500 and m is from 5 to 18.

15. The lead of embodiment 14 wherein n is from 20 to 1500 and m is 10 to 18.

16. The lead of any of embodiments 1 through 9 wherein the silicone-urethane polymer is prepared from a polydimethyl siloxane diol monomer of the formula:

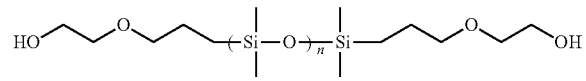

wherein n is from 10 to 1500.

17. The lead of any of embodiments 1 through 9 wherein the silicone-urethane polymer is prepared from a PDMS diol with hydrophobic end groups/blocks.

18. The lead of embodiment 17 wherein the PDMS diol with hydrophobic end groups are prepared from a hydride-terminated siloxane and an unsaturated alcohol selected from the group of 9-decen-1-ol, 10-undecen-1-ol, oleyl alcohol, and combinations thereof.

19. The lead of any of embodiments 1 through 9 wherein the silicone-urethane polymer is prepared from a hydrophobic co-soft segment and/or chain extender.

20. The lead of any of embodiments 1 through 19 wherein the silicone-urethane polymer is crosslinked.

21. The lead of any of embodiments 1 through 20 as dependent on embodiment 3 wherein the conductor is a coiled conductor.

EXAMPLES

Reference Polymer X

Reference Polymer X is a silicone polyurethane with a soft and hard segment weight ratio of 60/40, respectively, with the soft segment containing 80 wt-% PDMS (molecular weight approximately 1000 Da, n=10-11 repeat units) and 20 wt-% PTMO (poly(tetramethylene oxide), molecular weight approximately 1000 Da) and the hard segment comprised of BDO (1,4-butanediol) and MDI (4,4'-methylene diphenyl diisocyanate).

Reference Polymer Y

Reference Polymer Y is a silicone polyurethane with a soft and hard segment weight ratio of 60/40, respectively, with the soft segment containing 80 wt-% PDMS (molecular weight approximately 1000 Da, n=10-11 repeat units) and 20 wt-% PHMO (poly(hexamethylene oxide), molecular weight approximately 700 Da) and the hard segment comprised of BDO (1,4-butanediol) and MDI (4,4'-methylene diphenyl diisocyanate).

Method of Evaluating Hydrolytic Stability

Hydrolytic stability of various polymers is determined by monitoring the molecular weight changes of the polymer upon exposure to water and determining the kinetics of the hydrolysis reaction. The number average molecular weight (Mn) is directly related to the concentration of polymer species chain ends and consequently is a useful parameter for determining reaction kinetics (rates of reactions). For chemical degradation processes that result in chain scission, for example hydrolysis, the parameter 1/Mn is directly proportional to the concentration of chain ends, which increase as the chain scission reaction proceeds. The hydrolysis rate is typically constant as the concentrations of susceptible bonds and absorbed water are relatively constant until the late stages of hydrolysis, where the polymer typically exhibits significant water uptake and possibly dissolution, consequently a plot of 1/Mn with time would give a straight line with the slope representing the rate (Lyu, S. et al, "Kinetics and Time-Temperature Equivalence of Polymer Degradation," Biomacromolecules, 8, 2301-11 (2007); and Kole, S. et al., "Accelerated hydrothermal weathering of silicone rubber, EPDMS, and their blends," J. Applied. Polym. Sci., 54, 1329-1337 (1994)).

In order to isolate the hydrolysis reaction, oxygen should be eliminated from the environment to reduce the probability of any oxidation reactions. An inert gas such as nitrogen could be used for this purpose, for example bubbling nitrogen through aqueous solutions. The pH of the test solution should be controlled as hydrolysis reactions can be catalyzed by low or high pH, for example employing a buffered salt solution such as PBS (Phosphate Buffered Saline) with pH 7.4 (body pH). In order to permit experiments to be performed over a relatively short time frame and facilitate extrapolation of results exceeding the test duration, multiple elevated temperatures should be considered including the use condition temperature, for example, 37° C. The use of multiple temperatures including the use condition temperature would ensure that alternative degradation pathways are not occurring within the temperature range of the experiments via an Arrhenius analysis. The hydrolysis reaction could be monitored at various time points for each temperature and a 37° C. master curve established using time-temperature equivalence, the slope of which would give the hydrolysis rate and allow extrapolation to longer time periods.

At the various time points, samples are taken to determine molecular weight via SEC (Size Exclusion Chromatography). Further sample formats could be selected that would permit suitable evaluation of other pertinent parameters including mechanical properties (for example tensile properties).

Figure 6:
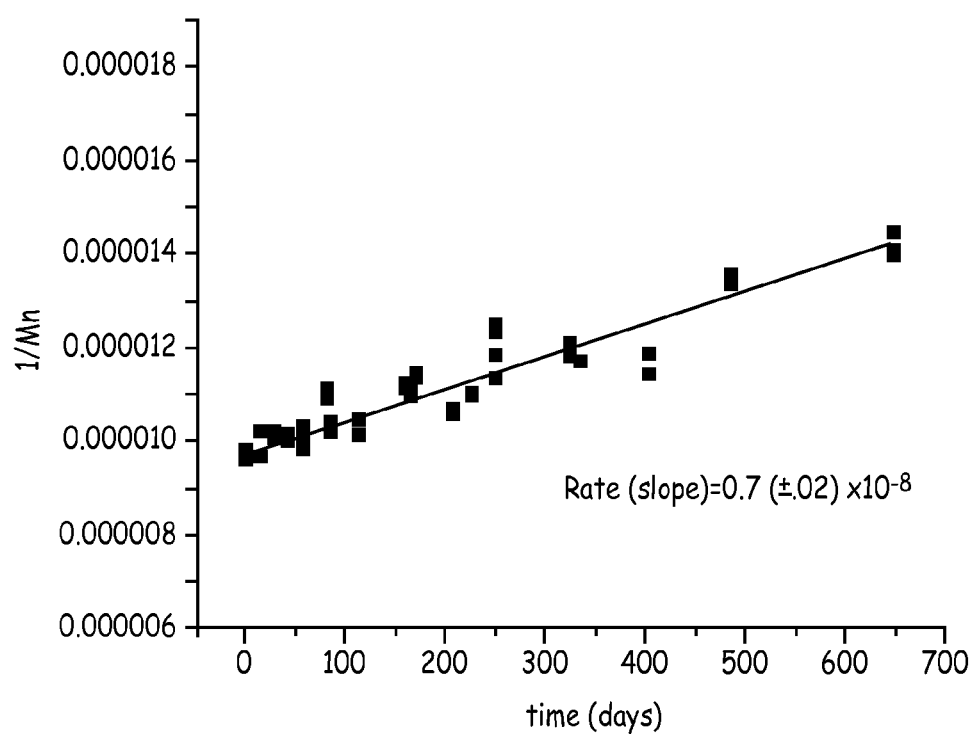
FIG. 6 is a 37° C. master curve showing the hydrolysis kinetics of a silicone polyurethane 'Polymer X.'

A 37° C. master curve showing the hydrolysis kinetics of Reference Polymer X is depicted in FIG. 6 via a reciprocal number average molecular weight plot with the rate constant given by the slope of the straight line.

Example 1

This example demonstrates a hydrolysis mechanism and its general catalysis for both a commercially available silicone polyurethane polymer and the PDMS diol precursor used in its preparation, with the formation and identification of lower molecular weight silanol hydrolysis products not present in the starting materials via GC-MS and NMR techniques. For example, after subjecting the silicone polyurethane and the PDMS diol precursor to elevated temperature in deionized (DI) water or phosphate buffered saline (PBS) buffer (up to 85° C., 1-6 weeks), GC-MS of the aqueous phase showed the presence of water-soluble hydrolysis products consisting of small oligomer units dimethylsilanediol (MDM) and tetramethyldisilanediol ($MD_2M$). These products were further confirmed by GC-MS after trimethylsilylation derivatization of the hydroxyl groups using BSTFA. Derivatization and GC-MS of the PDMS phase for the PDMS diol hydrolysis reaction showed the presence of non-water soluble hydrolysis products including hexamethyltrisilanediol ($MD_3M$), octamethyltetrasilanediol ($MD_4M$) and higher PDMS oligomer hydrolysis products.

Further, the PDMS hydrolysis reaction could be catalyzed by acid or base. Briefly, one hundred (100) μL of PDMS (molecular weight 1000 Da, dimethyl or alkyl ether diol terminated) were mixed with 1.3 mL of tetrahydrofuran, and 100 μL of NaOH solution (50 mM) was added to hydrolyze the polymer. The homogenous reaction mixture was placed into an NMR tube at room temperature. $^{29}$Si-NMR spectra were recorded at different time points. Over time, new peaks corresponding to the hydrolyzed products were observed. Peaks from −19 ppm to −21 ppm corresponded to Si in the main chain PDMS, and their intensity were used to indicate the hydrolysis rate. In a similar experiment, $H_2SO_4$ (100 mM) was also used to replace the NaOH solution for the acid-catalyzed hydrolysis experiment. In both experiments, the silicone NMR signal decreased from the PDMS main chain, indicating the progressive hydrolysis reaction. The hydrolyzed polymers were further analyzed by GC-MS after trimethylsilylation of the hydroxyl groups using BSTFA (N,O-bis(trimethylsilyl)trifluoroacetamide) and TMCS (trimethylchlorosilane). The GC-MS chromatograms clearly showed that the PDMS was hydrolyzed into small oligomer units such as dimethylsilanediol (MDM), tetramethyldisilanediol ($MD_2M$), and octamethyltetrasiloxane ($D_4$).

Further hydrolysis studies were conducted on a model compound that contained the unique ether and urethane linkages and the siloxane bonds introduced in the silicone-urethane copolymers. The chemical structure of the PDMS-polyurethane model compound is shown below.

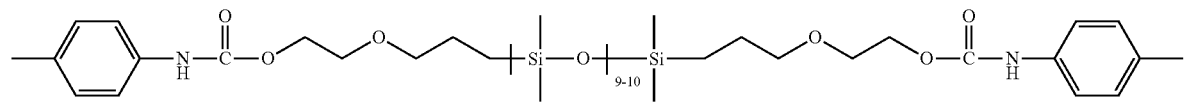

To synthesize the model compound, the PDMS diol utilized in the silicone-polyurethanes was reacted with 4-methylphenyl isocyanate. Bis(hydroxyethoxypropyl)polydimethylsiloxane (molecular weight—1000 Da) (299.2 mg, 0.243 mmol) was dissolved in chloroform (1 mL) and 4-methylphenyl isocyanate (76.674/80.97 mg, 0.519) was added. The reaction mixture sat undisturbed for one week. Liquid chromatography was used to purify the reaction products. The reaction products were eluted in 20% ethyl acetate/80% hexanes. A 10 g column was run on the Biotage automated column using these TLC measurements. The first fraction was placed into a 100 mL round bottom flask and evaporated to remove the solvent. A proton NMR was conducted in $CDCl_3$ and showed the desired product was obtained. $^1$H NMR (THF-d8, 400 MHz, ppm): δ 8.66 (s, 2H), 7.33 (d, J=8.5 Hz, 4H), 7.00 (d, J=8.4 Hz, 4H), 4.17 (t, J=4.8 Hz, 4H), 3.56 (overlay, 4H), 3.39 (t, J=6.6 Hz, 4H), 2.23 (s, 6H), 1.59 (p, J=7.5 Hz, 4H), 0.58 (m, 4H), −0.09-0.24 (m, 77H).

Figure 7:
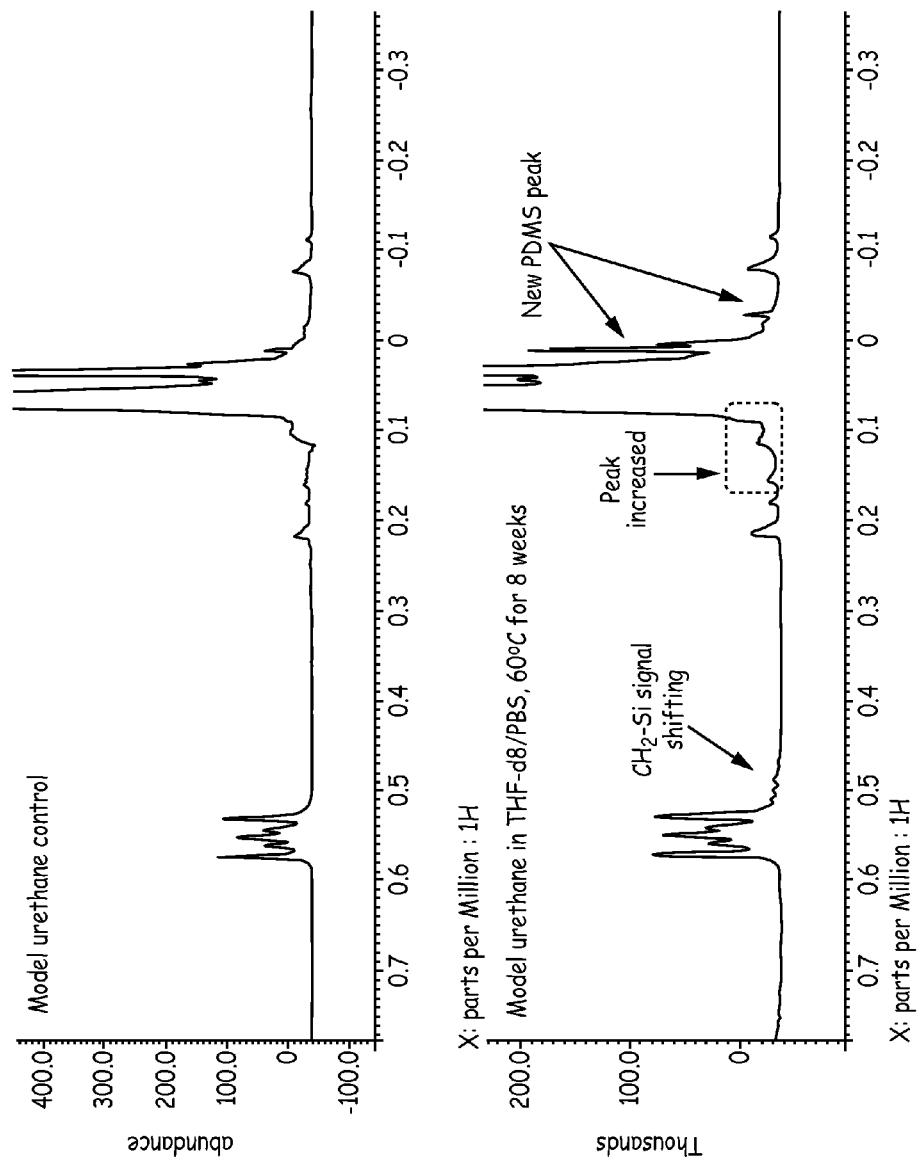
FIG. 7 is a proton NMR spectrum of the model compound control (top) and the model compound after 8 weeks at 60° C. (bottom).
Figure 8:
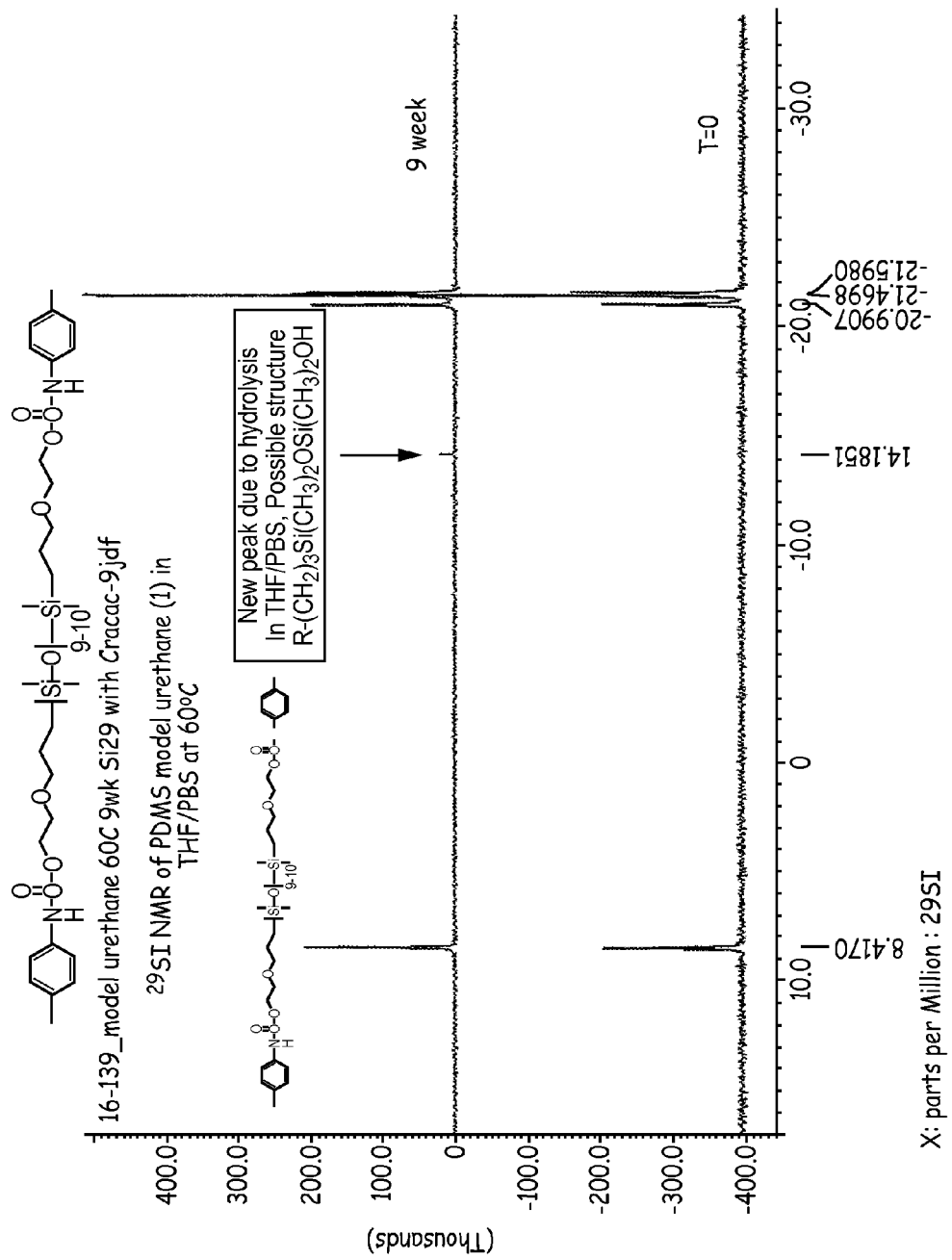
FIG. 8 is an $^{29}$Si NMR spectra of the model compound after 9 weeks at 60° C. (top spectrum) compared to the time zero model compound (bottom spectrum). A new peak at −14.2 ppm appeared in the hydrolyzed sample due to the formation of Si—OH.

The hydrolysis study was conducted by dissolving the model PDMS urethane compound (64 mg) in a miscible solution comprised of 3.2 mL THF-d8 and 0.25 mL PBS (pH 7.4). The solution was stored at 60° C. to increase the reaction kinetics. NMR spectra were acquired at room temperature to monitor the reaction. After 8 weeks at 60° C., the peak in the $^1$H NMR spectrum corresponding to the methylene next to the first siloxane shifted and new PDMS peaks were observed (FIG. 7). After 9 weeks at 60° C., a new peak was observed in the $^{29}$Si spectrum at −14.2 ppm, corresponding to $Si(CH_3)_2$—OH (FIG. 8).

All these results lead to the conclusion that the major degradation mechanism in silicone-polyurethane is siloxane hydrolysis.

Example 2

Figure 9:
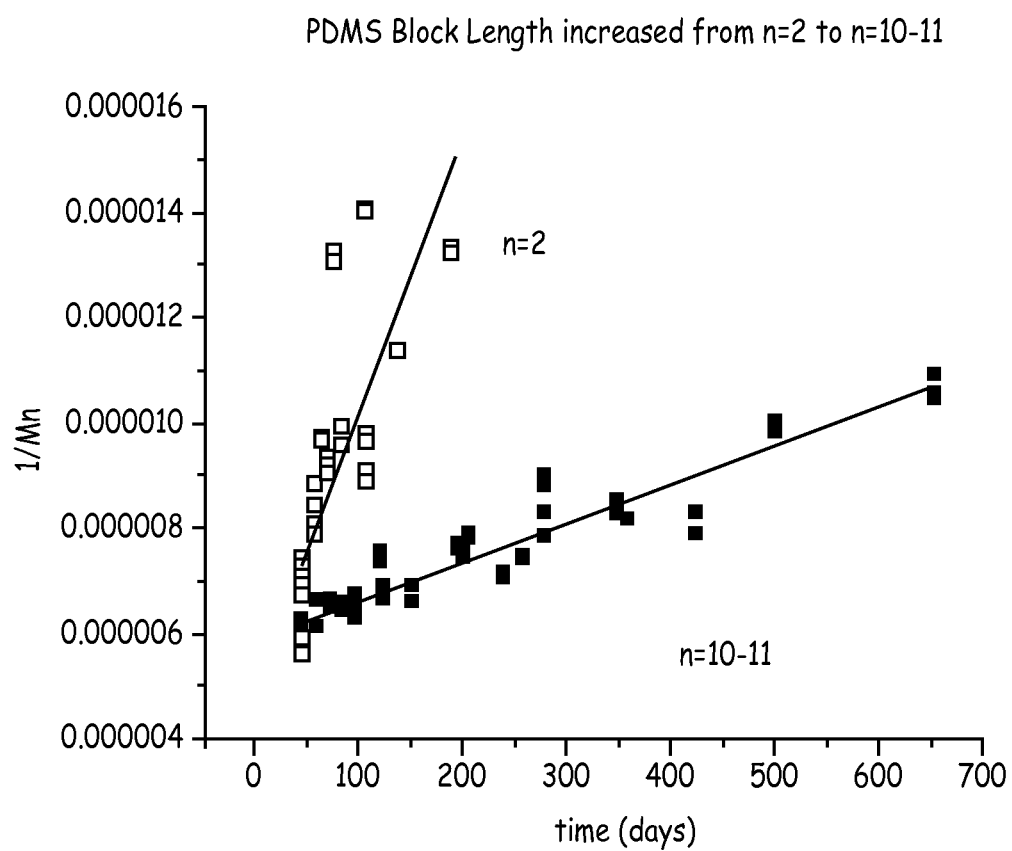
FIG. 9 is a 37° C. master curve showing the hydrolysis kinetics of two silicone polyurethane polymers made with different PDMS chain lengths (n=2 and n=10 PDMS repeat units respectively). The silicone polyurethane with PDMS chain length n=10-11 is the same composition as shown in FIG. 6 ('Polymer X'), whereas the silicone polyurethane with chain length n=2 does not contain PTMO and similarly contains BDO and MDI.

Synthesis of Silicone-Polyurethane Using PDMS Diol with Molecular Weight Equal to or Higher than 1000 Da Silicone polyurethane synthesized with longer PDMS chains showed slower degradation due to hydrolysis. FIG. 9 shows that the polyurethane made with short chain PDMS (repeat unit n=2) was hydrolyzed at a much faster rate than polyurethane made with longer PDMS (repeat unit n=10-11, molecular weight approximately 1000 Da).

Using PDMS with molecular weight higher than PDMS molecular weight approximately 1000 Da (n=10-11 repeat units) to synthesize polyurethane results in increased hydrolytic stability.

Synthesis of PDMS Diol with High Molecular Weight

Hydride-terminated PDMS is purchased from Gelest (Product number: DMS-H21) or synthesized by the acid catalyzed ring-opening polymerization (Polym. Mat. Sci. Eng. 1984, 50, 518). These PDMS should have a molecular weight ranging from 1000 to 100,000 Da. The hydride-terminated PDMS is then reacted with, for example, allyloxy ethanol (Aldrich). Briefly, to a 3-neck round-bottom flask, hydride-terminated PDMS is added under nitrogen. The alkoxy ethanol is then added dropwise through an addition funnel with Karstedt's catalyst. The reaction is kept at 70-80° C. for another hour. The catalyst is removed from the polymer by charcoal treatment and further purified.

The PDMS diol structure:

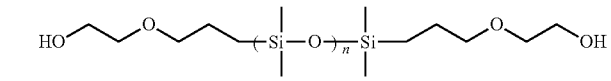

wherein 10<n<1500.

Synthesis of Polyurethane Using PDMS Diol with Molecular Weight Equal or Higher than 1000 Da.

Polyurethane can be synthesized by a two-step method or one-step method. The following is an example of procedure for the one-step bulk polymerization.

A mixture of dried PDMS diol and 1,4-butanediol (BDO) is charged into a polypropylene beaker and degassed under vacuum at 80° C. After the catalyst (dibutyltin dilaurate) is added in at 70° C. under nitrogen atmosphere, dried MDI is quickly added with rapid stirring. The viscous mixture is poured into a TEFLON beaker and cured under nitrogen at 100° C. overnight. Polyurethane is obtained after the temperature is cooled to room temperature. There are other ways to make this. One strategy is to include all the MDI first, then add the PDMS, and then the BDO.

Alternatively, a two-step method can be used. For example, dried MDI is charged to a round-bottomed flask, melted and heated to 70° C. with agitation under a nitrogen atmosphere. Dried PDMS diol is added dropwise and the reaction allowed to proceed for a further hour prior to transferring to a TEFLON beaker. Subsequently, 1,4-butanediol is added rapidly with or without catalyst (dibutyltin dilaurate or stannous octoate) accompanied by vigorous stirring. The mixture is heated at 100° C. overnight to complete the reaction before cooling to room temperature.

Example 3

Polysiloxane with Alternative Side Groups

Another approach to slow down the hydrolysis of the siloxane bond in silicone polyurethane is to synthesize polyurethane with polysiloxane other than PDMS. Examples will be some polysiloxane homopolymers such as polydiethylsiloxane, polypropylsiloxane, polydibutylsiloxane, etc., and copolymers of these species. These polysiloxane contain bulky side groups and could provide the steric hindrance to retard or stop the hydrolysis reaction. Some structures are shown below:

Homopolymer Examples

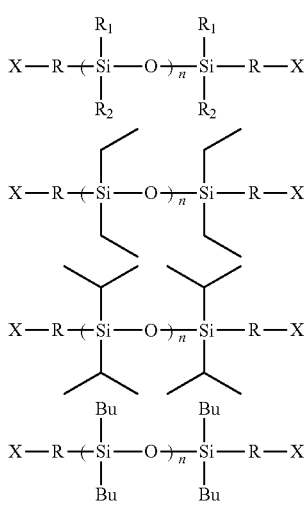

X = hydroxyl or amine group

Copolymer Examples

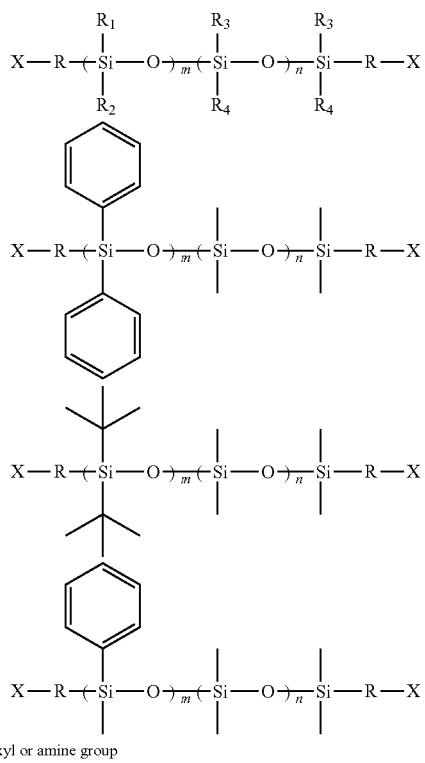

X = hydroxyl or amine group

These polymers can be synthesized by acid catalyzed ring-opening polymerization of the corresponding cyclic monomers to make the hydride functional polymers, followed by hydrosilylation as described before. In the above homopolymer and copolymer exemplary structures, typical values of n are from 10 to 1500, typical values of m are from 1 to 1000, and R is a divalent ether-containing chain or an alkyl chain.

Examples 4 and 5

Synthesis of Silicone-Polyurethane with Increased Hydrophobicity

Another approach to slow down the hydrolysis of silicone-polyurethane is to increase the overall hydrophobicity of the polyurethane. Specifically, to reduce the local water concentration near the PDMS moiety. Following are two approaches employed to increase the hydrophobicity of soft segment domain.

Example 4A

Introducing Hydrophobic Moieties into Polyurethane at PDMS Chain Ends to Slow Down Hydrolysis In addition to introducing hydrophobic moieties into the silicone polyurethane via the PDMS chain ends to slow hydrolysis, the example given below further substitutes the alkyl ether functionality in the PDMS utilized in commercial silicone polyurethanes that could participate in facilitating/catalyzing siloxane hydrolysis.

PDMS diol used in commercially available silicone polyurethanes typically have the structure:

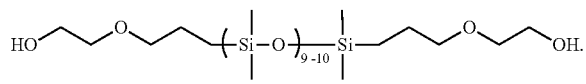

Further, by increasing the alkyl chain length (m) in the structure below could decrease the proximity of the neighboring urethane functionality from the siloxane ether bonds, as this functionality may also participate in facilitating siloxane ether hydrolysis.

The modified PDMS structure:

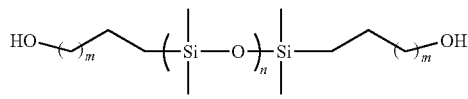

wherein n is from 10 to 1500 and m is from 0 to 18.

Two model polyurethane-PDMS compounds were synthesized using the diol utilized in the synthesis of silicone-polyurethane copolymers and a modified diol that replaced the ether oxygen with a methylene, such that m=4 and n=9-10 in the structure shown above. The modified diol was synthesized via hydrosilyation through the platinum-catalyzed reaction of H—$(Si(CH_3)_2$—O$)_{9-10}$—$Si(CH_3)_2$—H and 5-hexen-1-ol. Each diol was reacted with 4-methylphenyl isocyanate to create the urethane linkage as described in Example 1. The chemical structures of the two model compounds studied for siloxane hydrolysis rates are shown below.

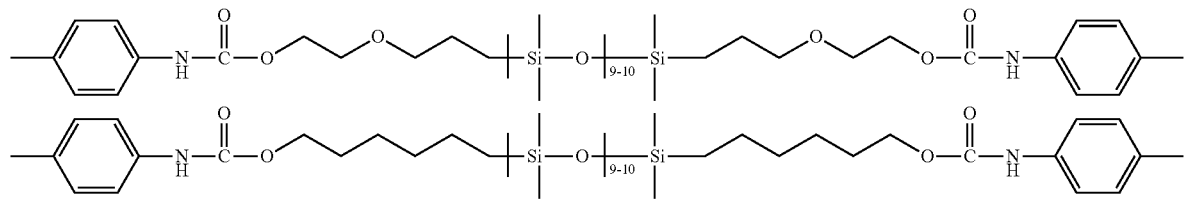

Figure 10:
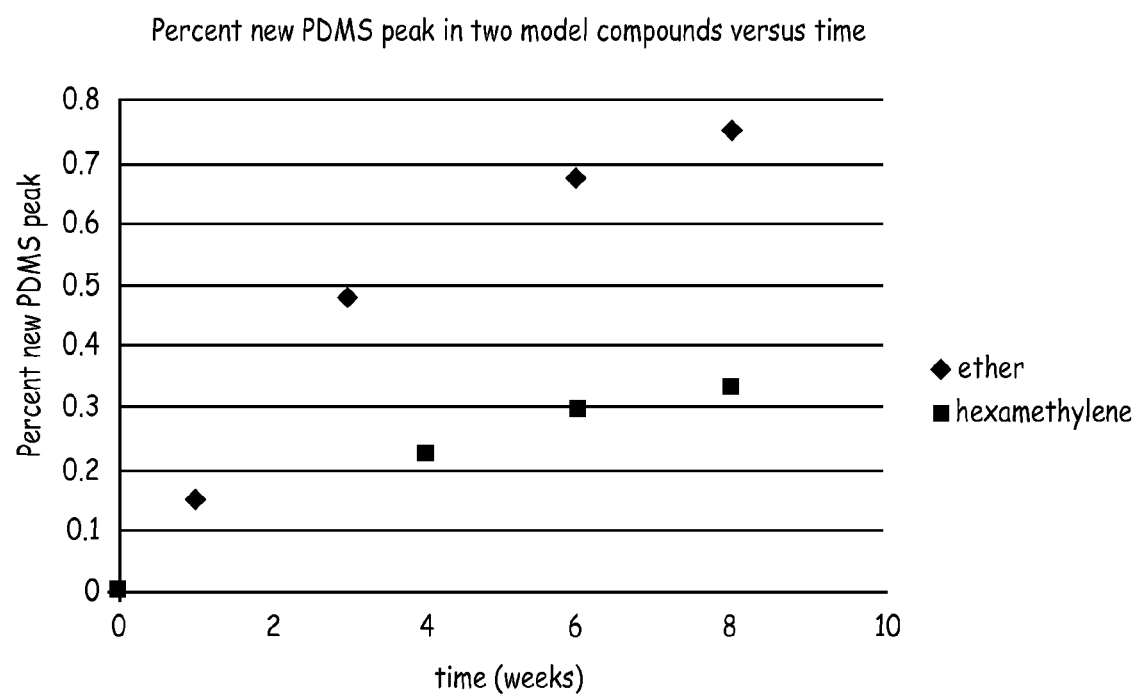
FIG. 10 is a graph of the percent new PDMS peak versus time for an ether-containing model compound and a hexamethylene model compound.

The siloxane hydrolysis rates of the two model PDMS urethane compounds were studied by NMR. The model compounds (64 mg) were dissolved in a miscible solution comprised of 3.2 mL THF-d8 and 0.25 mL PBS (pH 7.4). The solutions were stored at 60° C. Proton NMR spectra were acquired at room temperature to monitor the reaction. The formation of a new PDMS peak at −0.01 ppm was quantified by integration. The percent new PDMS peak was calculated by dividing the integral of the new peak at −0.01 ppm with the integral of all the PDMS peaks multiplied by 100. The percent new PDMS peak was plotted versus time in FIG. 10.

Figure 11:
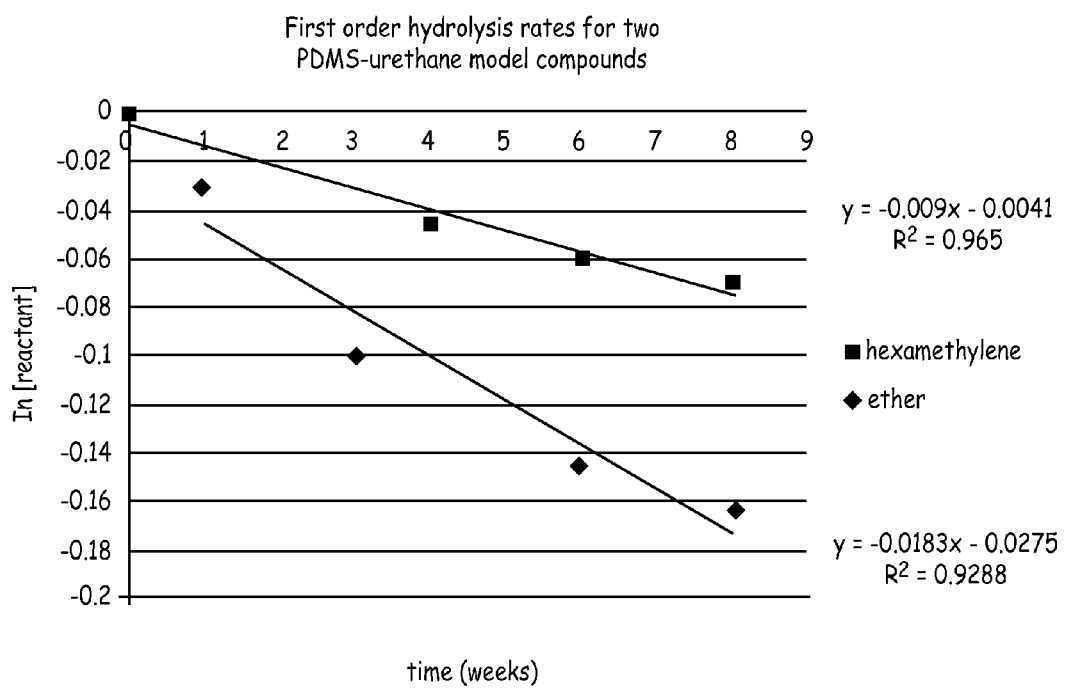
FIG. 11 is a plot of the first order hydrolysis rates for two polyurethane-PDMS model compounds.

The kinetics of the hydrolysis reaction was evaluated using the first order rate equation. A plot of the natural log of the concentration of reactants versus time was created and the hydrolysis rate was determined from the slope of the line (FIG. 11).

The hydrolysis rate of the ether-containing model compound was 0.0183 s$^{-1}$. The hydrolysis rate of the hexamethylene model compound was 0.009 s$^{-1}$.

Therefore, replacing the ether-containing end group with a hydrophobic hexamethylene end group reduced the rate of siloxane hydrolysis by half.

Synthesis of PDMS Diol with Hydrophobic End Groups

The intermediate hydride-terminated siloxane is purchased from Gelest (Product number: DMS-H21) or synthesized by the acid catalyzed ring-opening polymerization (Polym. Mat. Sci. Eng. 1984, 50: 518). The hydride-terminated siloxane is then reacted with a serial of unsaturated alcohol such as: 9-decen-1-ol, 10-undecen-1-ol, or oleyl alcohol. These hydrophobic alcohols can be purchased from Aldrich.

Structure of the Unsaturated Alcohol 9-decen-1-ol: $H_2C=CH(CH_2)_7CH_2OH$
10-undecen-1-ol: $H_2C=CH(CH_2)_8CH_2OH$
Oleyl alcohol: $CH_3(CH_2)_7CH=CH(CH_2)_7CH_2OH$ Briefly, to a 3-neck round-bottom flask, hydride-terminated siloxane is added under nitrogen. The 9-decen-1-ol is then added dropwise through an addition funnel with Karstedt's catalyst. The reaction is kept at 70-80° C. for another hour. The catalyst is removed from the polymer by charcoal treatment and further purified with thin film evaporator.

Synthesis of Polyurethane Using the PDMS Diol with Hydrophobic End Groups

Polyurethane can be synthesized by a two-step method or one-step method. The following is an example of procedure for the two-step bulk polymerization.

Dried MDI is charged to a round-bottomed flask, melted and heated to 70° C. with agitation under a nitrogen atmosphere. Dried PDMS diol is added dropwise and the reaction allowed to proceed for a further hour prior to transferring to a TEFLON beaker. Subsequently, 1,4-butanediol is rapidly added with/without catalyst (dibutyltin dilaurate or stannous octoate) accompanied by vigorous stirring. The mixture is heated at 100° C. overnight to complete the reaction before cooling to room temperature.

Example 4B

Introducing Hydrophobic Moieties into Polyurethane at PDMS Chain Ends to Slow Down Hydrolysis 1.1 Synthesis of PMDS-C6-diol

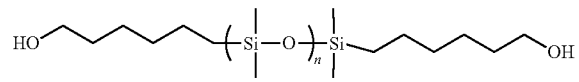

Hydride terminated PDMS (51 gram, 0.045 mol) was mixed with 5-hexen-1-ol (10.4 g, 0.1 mol) in 80 ml toluene. 2.1 mL of chloroplatinic acid solution was added and the reaction mixture was heated to reflux overnight. After cooling to RT, 100 mL of heptane was added and organic layer was wash with water for 5 times, and then dried over magnesium sulfate. The excess 5-hexen-1-ol was removed by distillation and 59 grams of PDMS-C6-diol is obtained as clear oil (yield 95%). $^1$H-NMR was used to characterize the PDMS-C6-diol. $^1$H NMR (CDCl$_3$, 400 MHz) δ 3.62 (t, 4H), 1.55 (m, 4H), 1.45 (broad, 2H), 1.33 (m, 12H), 0.52 (t, 4H), 0.04 (m, 96H).

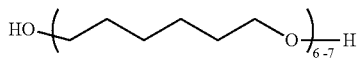

1.2 Synthesis of PHMO

PHMO was synthesized by acid catalyzed condensation method. Briefly, 100 g of 1,6-hexan-diol was heated to 170° C. in the presence of concentrated sulfuric acid. Polymerization is monitored by 1H-NMR and stopped when targeted molecular weight is obtained. PHMO with molecular weight (Mn by NMR) of 620 was synthesized.

1.3 Synthesis of PDMS-C6-polyurethane

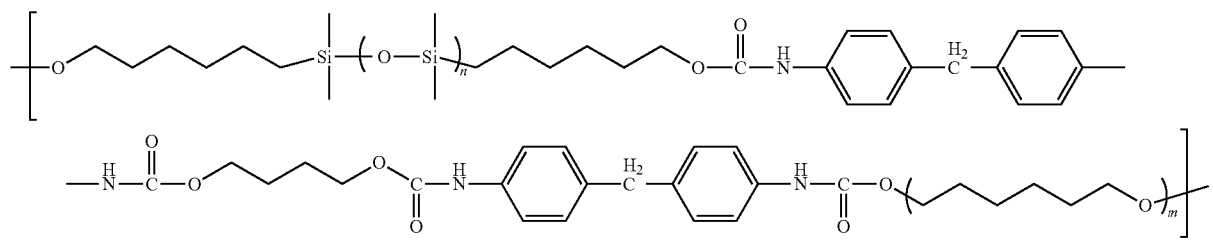

PDMS-C6-diol (5 g, 3.65 mmol) synthesized was mixed with PHMO diol (1.29 g, 2.08 mmol) in 50 mL of THF and 50 mL of DMF mixture. The solution was heated to 65° C. and 3.2 g of MDI was added with DBTDL as catalyst. After 1 hour, 0.63 g of 1,4-butanediol was added as chain extender. The reaction continued 50° C. overnight. Polyurethane was obtained by precipitating into methanol solution. Evidence the polyurethane was made was provided by NMR and GPC data.

Example 5

Introducing Hydrophobic Segment to Slow Down Hydrolysis

Another way to increase the hydrophobicity of polyurethane is to use hydrophobic co-soft segment and/or chain extender. Following are some diols that can be used as the co-soft segment/chain extender to prepare polyurethane with PDMS.

Amorphous Hydrophobic Telechelic Hydrocarbon Diols

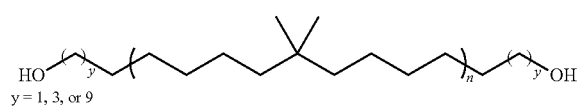

Amorphous Hydrophobic Telechelic Hydrocarbon Diol

These amorphous, hydrophobic telechelic hydrocarbon diols (wherein n is from 1 to 30) can be synthesized using acyclic diene metathesis (ADMET) polymerization (Benz et al., U.S. Pat. No. 7,101,956; Macromolecular Chemistry and Physics, 2009, 210 (21): 1818-1833.). The hydrocarbon backbone is based on a mimic of an ethylene/isobutylene polymer, made by the ADMET polymerization of a gem-dimethyl substituted α,ω-diene followed by hydrogenation of the polymer's repeat unit unsaturation. Chain termination reactants (CTR's) having one, three, and nine methylene "spacers," respectively, between their olefin and alcohol precursor group are used to cap the polymer chain ends to yield 2.0 functional telechelics. Use of the medium length CTR in a polymerization-depolymerization scheme, results in amorphous (Tg=−56° C.) telechelic diols with good molecular weight control.

PIB-Diol

The structure of PIB diol is shown below (wherein n is from 5 to 50), a'nd it can be prepared by cationic polymerization of isobutylene and further chain-end modification, which is described in the method of International Pub. No. WO 2008/066914.

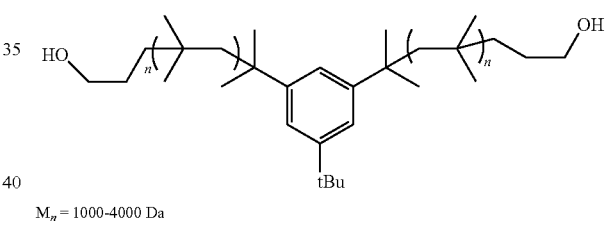

$M_n$ = 1000-4000 Da

Aliphatic Diols

Aliphatic diols made from natural products, such as C19-diol and dimer diol, have been prepared and used in the industry with large scale. C19-diol can be synthesized from oleyl alcohol by hydroformylation and reduction (U.S. Pat. No. 4,243,818). Dimer diol (C36-diol, wherein x+y=33 and m+n=33) can be synthesized by dimerization of fatty acid and followed by hydrogenation. This type of diol also offers hydrophobicity and can be used with PDMS as a soft segment and/or chain extender to synthesize polyurethane.

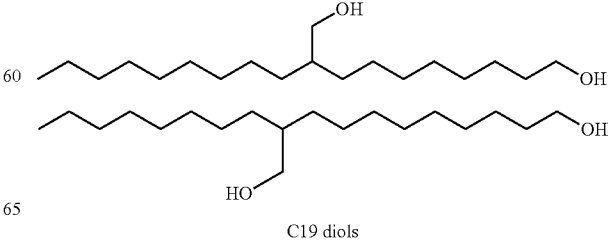

C19 diols

-continued

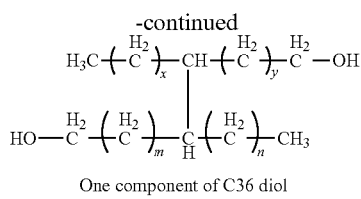

One component of C36 diol

Fluorinated Telechelic Diol

A fluorinated telechelic diol with structure shown below can be synthesized according to the literature (Journal of Fluorine chemistry, 2001(107): 81-88). It can be used to synthesize polyurethane with PDMS to increase the hydrophobicity as a co-soft segment or chain extender.

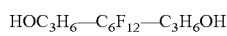

Disilane Diol

A silane diol with structure shown below can be prepared according to Benz's method (U.S. Pat. Pub. No. 2004/0054113). And it also can be used to prepare polyurethane with PDMS.

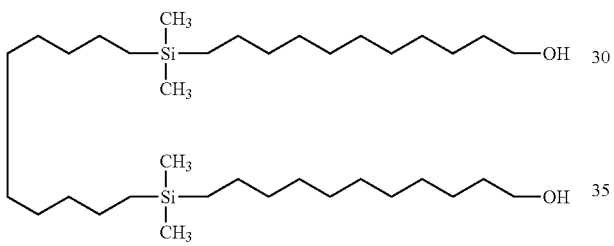

Example of Procedure for the One-Step Bulk Polymerization.

Polyurethane can be synthesized by a two-step method or one-step method, and following is an example of procedure for the one-step bulk polymerization.

A mixture of dried PDMS diol, PIB diol, and 1,4-butanediol is charged into a polypropylene beaker and degassed under vacuum at 80° C. After the catalyst (dibutyltin dilaurate) is added in at 70° C. under nitrogen atmosphere, dried HMDI is quickly added with rapid stirring. The viscous mixture is poured into a Teflon beaker and cured under nitrogen at 100° C. overnight. Polyurethane is obtained after the temperature is cooled to room temperature.

The hydrophobicity of the hard segment in silicone-polyurethane can also be increased by replacing the conventional chain extender 1,4-butandiol with 1,6-hexanediol, 1,7-heptanediol, 1,8-octanediol, 1,9-nonanediol, 1,10-decanediol, and the hydrophobic diols described above.

Example 6

Biostable Silicone Polyurethane with Crosslinked Soft Segment

Crosslinked materials are mechanically stable due to their networked structure. For example, silicone adhesive/sealant is mechanically stable for a long period time even in contact with water. In an analogous manner to this phenomenon, silicone-polyurethane with crosslinked polysiloxane moiety should have longer mechanical stability than that without crosslinking.

One approach to crosslink PDMS is to use radical reaction, similar to the crosslinking method used in the silicone tubing. Since the polyurethane tubing is extruded at high temperature, a radical generator such as dicumyl peroxide, Di-t-amyl peroxide, and Di-t-butyl peroxide will be used to crosslink the PDMS domain in the polyurethane. During the extrusion, a small percentage of the peroxide is introduced into the polyurethane and mixed in the extruder. These peroxides decompose at high temperature and have reasonable half-lives at 150-160° C. This allows the PDMS domain to be crosslinked while the polyurethane is being extruded. Post-extrusion cure is possible if necessary. Other radical generator could be used if those mentioned above do not give desired crosslink density.

Alternatively, a vinylmethylsiloxane-dimethylsiloxane copolymer (structure shown below) can be introduced to facilitate the crosslink. These copolymers can be purchased from Gelest (product number: VDT-123 to VDT-954). A small percentage (5-10%) of the copolymer is blended with silicone-polyurethane during the extrusion, and the copolymer will go into the PDMS domain due to the phase separation. At high temperature, the soft segment containing the PDMS and vinylmethylsiloxane-dimethylsiloxane copolymer (structure shown below wherein m is from 1 to 100 and n is from 2 to 10) can be crosslinked with or without need of a radical initiator.

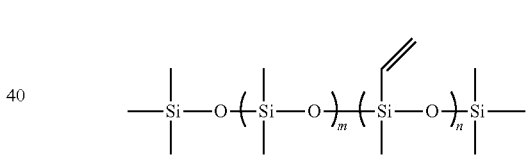

Another approach to crosslink the PDMS in the urethane is to prepare the silicone-polyurethane with polysiloxane copolymer containing crosslinkable units. These crosslinkable units will only react with each other at high temperature. For example, a copolymer of PDMS with multiple pendent benzocyclobutene (BCB) groups is used as a soft segment for making polyurethane. Due to the strained four-member ring, the BCB can be converted to o-xylylene at temperatures above 180° C., and react with itself to form an 8-member ring. This allows us to thermally process the polyurethane by extrusion or compression molding without premature cure. The crosslinked PDMS domain will maintain the mechanical properties longer than the non-crosslinked version upon the same degree of degradation (mainly hydrolysis). Additionally, the hydrophobic BCB group will decrease the water absorption in the polyurethane, which in turn slows down the hydrolysis reaction.

By controlling the content of BCB in the polysiloxane oligiomer, the crosslinking density can be controlled.

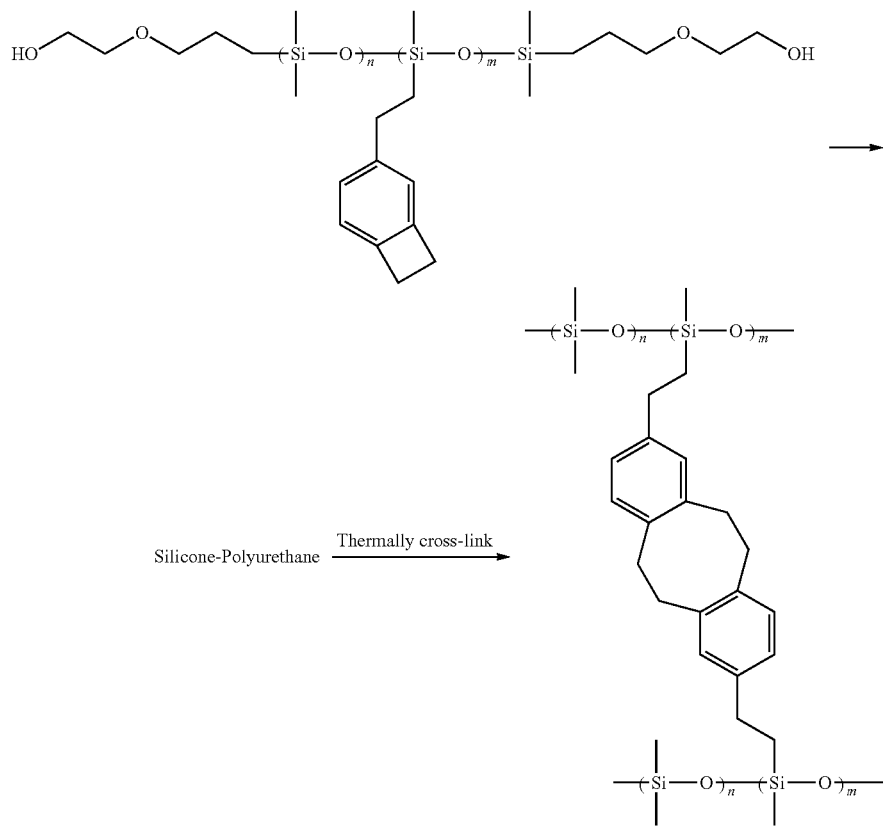

wherein m is from 2 to 10 and n is from 10 to 1500.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. A medical lead comprising an elongated lead body comprising a polymeric material, wherein the polymeric material consists of a silicone-urethane polymer having hydrolytic stability greater than that of a Reference Polymer X, a Reference Polymer Y, or both Reference Polymers X and Y;

wherein the silicone-urethane polymer and at least one of Reference Polymer X and Reference Polymer Y are tested under same conditions of controlled pH, temperature, inert gas, and aqueous solution according to Method of Evaluating Hydrolytic Stability to identify the silicone-urethane polymer having hydrolytic stability greater than that of Reference polymer X, Reference Polymer Y, or both Reference Polymers X and Y;

wherein Reference Polymer X is a silicone polyurethane with a soft and hard segment weight ratio of 60/40, respectively, with the soft segment containing 80 wt-% PDMS (molecular weight approximately 1000 Da, n=10-11 repeat units) and 20 wt-% PTMO (poly(tetramethylene oxide), molecular weight approximately 1000 Da) and the hard 15 segment comprised of BDO (1,4-butanediol) and MDI (4,4'-methylene diphenyl diisocyanate); and wherein Reference Polymer Y is a silicone polyurethane with a soft and hard segment weight ratio of 60/40, respectively, with the soft segment containing 80 wt-% PDMS (molecular weight approximately 1000 Da, n=10-11 repeat units) and 20 wt-% PHMO (poly(hexamethylene oxide), molecular weight approximately 700 Da) and the hard segment comprised of BDO (1,4'-butanediol) and MDI (4,4'-methylene diphenyl diisocyanate).

2. The medical lead of claim 1 in the form of a medical electrical or neurological lead.

3. A medical electrical lead comprising:

an elongated lead body having a first lumen, extending longitudinally along said lead body; and a conductor located within and extending longitudinally along said lumen;

wherein the lead body consists of a polymeric material, wherein the polymeric material comprises a silicone-urethane polymer having hydrolytic stability greater than that of a Reference Polymer X, a Reference Polymer Y, or both Reference Polymers X and Y;

wherein the silicone-urethane polymer and at least one of Reference Polymer X and Reference Polymer Y are tested under same conditions of controlled pH, temperature, inert gas, and aqueous solution according to Method of Evaluating Hydrolytic Stability to identify the silicone-urethane polymer having hydrolytic stability greater than that of Reference Polymer X, Reference Polymer Y, or both Reference Polymers X and Y;

wherein Reference Polymer X is a silicone polyurethane with a soft and hard segment weight ratio of 60/40, respectively, with the soft segment containing 80 wt-% PDMS (molecular weight approximately 1000 Da, n=10-11 repeat units) and 20 wt-% PTMO (poly(tetramethylene oxide), molecular weight approximately 1000 Da) and the hard 15 segment comprised of BDO (1,4-butanediol) and MDI (4,4'-methylene diphenyl diisocyanate); and wherein Reference Polymer Y is a silicone polyurethane with a soft and hard segment weight ratio of 60/40, respectively, with the soft segment containing 80 wt-% PDMS (molecular weight approximately 1000 Da, n=10-11 repeat units) and 20 wt-% PHMO (poly(hexamethylene oxide), molecular weight approximately 700 Da) and the hard segment comprised of BDO (1,4'-butanediol) and MDI (4,4'-methylene diphenyl diisocyanate).

4. The lead of claim 3 wherein the polymeric material is polymeric insulation material.

5. The lead of claim 3 wherein the silicone-urethane polymer is derived from one or more polydialkyl-, polydiaryl-, or polyalkylaryl-siloxane monomers other than a polydimethylsiloxane monomer.

6. The lead of claim 3 wherein the silicone-urethane polymer is derived from a mixture of one or more polydimethylsiloxane monomers and at least one other monomer selected from polydialkyl-, polydiaryl-, and polyalkylaryl-siloxane monomers other than a polydimethylsiloxane monomer.

7. The lead of claim 3 wherein the silicone-urethane polymer is derived from a polydimethyl siloxane diol monomer with a number average molecular weight equal to or higher than 1000 Da.

8. The lead of claim 3 wherein the silicone-urethane polymer is derived from a polydimethyl siloxane diol monomer of the formula:

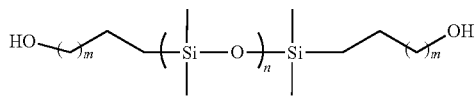

wherein n is from 10 to 1500 and m is from 0 to 18.

9. The lead of claim 8 wherein n is from 15 to 1500 and m is from 5 to 18.

10. The lead of claim 9 wherein n is from 20 to 1500 and m is 10 to 18.

11. The lead of claim 3 wherein the silicone-urethane polymer is derived from a polydimethyl siloxane diol monomer of the formula:

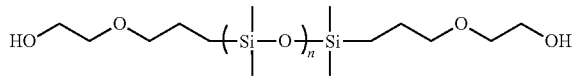

wherein n is from 10 to 1500.

12. The lead of claim 3 wherein the silicone-urethane polymer is derived from a PDMS diol with hydrophobic end groups/blocks.

13. The lead of claim 12 wherein the PDMS diol with hydrophobic end groups is derived from a hydride-terminated siloxane and an unsaturated alcohol selected from the group of 9-decen-1-ol, 10-undecen-1-ol, oleyl alcohol, and combinations thereof.

14. The lead of claim 3 wherein the silicone-urethane polymer is derived from a hydrophobic co-soft segment and/or chain extender.

15. The lead of claim 3 wherein the silicone-urethane polymer is crosslinked.

16. The lead of claim 3 wherein the conductor is a coiled conductor.

17. A medical, neurological lead for use in electrical signaling and/or drug delivery comprising:
an elongated body with a distal portion, a central portion and a proximal portion;
wherein the body includes delivery means extending to said distal portion; and
wherein the elongated body consists of a polymeric material, wherein the polymeric material comprises a silicone-urethane polymer having hydrolytic stability greater than that of a Reference Polymer X, a Reference Polymer Y, or both Reference Polymers X and Y;
wherein the silicone-urethane polymer and at least one of Reference Polymer X and Reference Polymer Y are tested under same conditions of controlled pH, temperature, inert gas, and aqueous solution according to Method of Evaluating Hydrolytic Stability to identify the silicone-urethane polymer having hydrolytic stability greater than that of Reference Polymer X, Reference Polymer Y, or both Reference Polymers X and Y;
wherein Reference Polymer X is a silicone polyurethane with a soft and hard segment weight ratio of 60/40, respectively, with the soft segment containing 80 wt-% PDMS (molecular weight approximately 1000 Da, n=10-11 repeat units) and 20 wt-% PTMO (poly(tetramethylene oxide), molecular weight approximately 1000 Da) and the hard 15 segment comprised of BDO (1,4-butanediol) and MDI (4,4'-methylene diphenyl diisocyanate); and
wherein Reference Polymer Y is a silicone polyurethane with a soft and hard segment weight ratio of 60/40, respectively, with the soft segment containing 80 wt-% PDMS (molecular weight approximately 1000 Da, n=10-11 repeat units) and 20 wt-% PHMO (poly(hexamethylene oxide), molecular weight approximately 700 Da) and the hard segment comprised of BDO (1,4'-butanediol) and MDI (4,4'-methylene diphenyl diisocyanate).

18. The lead of claim 17 wherein the delivery means comprises electrical signal delivery means.

19. The lead of claim 18 wherein the electrical signal delivery means is an implantable lead having at least one electrode.

20. The lead of claim 17 wherein the delivery means comprises drug delivery means.

21. The lead of claim 20 wherein the drug delivery means comprises a catheter.

22. The lead of claim 17 wherein the polymeric material is polymeric insulation material.

23. The lead of claim 17 wherein the silicone-urethane polymer is derived from one or more polydialkyl-, polydiaryl-, or polyalkylaryl-siloxane monomers other than a polydimethylsiloxane monomer.

24. The lead of claim 17 wherein the silicone-urethane polymer is derived from a mixture of one or more polydimethylsiloxane monomers and at least one other monomer selected from polydialkyl-, polydiaryl-, and polyalkylaryl-siloxane monomers other than a polydimethylsiloxane monomer.

25. The lead of claim 17 wherein the silicone-urethane polymer is derived from a polydimethyl siloxane diol monomer with a number average molecular weight equal to or higher than 1000 Da.

26. The lead of claim 17 wherein the silicone-urethane polymer is derived from a polydimethyl siloxane diol monomer of the formula:

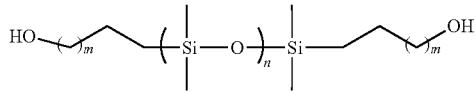

wherein n is from 10 to 1500 and m is from 0 to 18.

27. The lead of claim 26 wherein n is from 15 to 1500 and m is from 5 to 18.

28. The lead of claim 27 wherein n is from 20 to 1500 and m is from 10 to 18.

29. The lead of claim 17 wherein the silicone-urethane polymer is derived from a polydimethyl siloxane diol monomer of the formula:

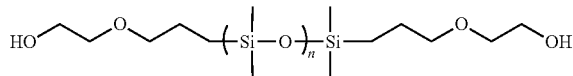

wherein n is from 10 to 1500.

30. The lead of claim 17 wherein the silicone-urethane polymer is derived from a PDMS diol with hydrophobic end groups/blocks.

31. The lead of claim 30 wherein the PDMS diol with hydrophobic end groups is derived from a hydride-terminated siloxane and an unsaturated alcohol selected from the group of 9-decen-1-ol, 10-undecen-1-ol, oleyl alcohol, and combinations thereof.

32. The lead of claim 17 wherein the silicone-urethane polymer is derived from a hydrophobic co-soft segment and/or chain extender.

33. The lead claim 17 wherein the silicone-urethane polymer is crosslinked.

* * * * *